US006277818B1

(12) United States Patent
Mazar et al.

(10) Patent No.: US 6,277,818 B1
(45) Date of Patent: Aug. 21, 2001

(54) CYCLIC PEPTIDE LIGANDS THAT TARGET UROKINASE PLASMINOGEN ACTIVATOR RECEPTOR

(75) Inventors: Andrew P. Mazar, La Jolla; Terence R. Jones, San Diego, both of CA (US)

(73) Assignee: Angstrom Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/181,816

(22) Filed: Oct. 29, 1998

(51) Int. Cl.$^7$ .......................... A61K 38/04; A61K 38/12; C07K 7/54
(52) U.S. Cl. .................. 514/9; 514/11; 530/317; 530/323; 424/1.69; 435/325
(58) Field of Search ................................ 530/317, 323; 514/9, 11

(56) References Cited

U.S. PATENT DOCUMENTS 5,656,726 * 8/1997 Rosenberg et al. ................ 530/326
5,679,782 * 10/1997 Rosenberg et al. ................ 536/23.1

FOREIGN PATENT DOCUMENTS

| 90/12091 | 10/1990 | (WO) . |
| 93/24141 | 12/1993 | (WO) . |
| 94/28145 | 12/1994 | (WO) . |
| 98/21230 * | 5/1998 | (WO) . |
| 98/46731 | 10/1998 | (WO) . |

OTHER PUBLICATIONS

Magdolen V et al: "Systematic Mutational Analysis of the Receptor–Binding Region of the Human Urokinase–Type Plasminogen Activator"; European Journal of Biochemistry, DE, Berling, vol. 237, Jan. 1, 1996 (1996–01–01), pp. 743–751, XP000652373 ISSN:0014–2956; cited in the application the whole document.

Burgle E.A.: "Inhibition of the action of urokinase–type plasminogen activator (uPA) with its receptor (UPAR) by synthetic peptides"; Biological Chemistry, vol. 378, Mar. 1997 (1997–03), pp. 231–237, XP000876916 the whole document.

Mazar, A.P. et al.: "High–affinity, small cyclic peptide urokinase plasminogen activator receptor (uPAR)–targeting ligands localize reporter and therapeutic conjugates to the surfaces of tumor cells and stimulated endothelial cells." Proceedings of the American Association for Cancer Research Annual Meeting, (Mar., 1999) vol. 40, pp. 22., XP002131000 the whole document.

Appella, E. et al., J. Biol. Chem., 262:4437–40 (1987).

Behrendt, N. et al., Biol. Chem. Hoppe–Seyler, 376:269–79 (1995).

Danø, K. et al., Adv. Cancer Res., 44:139–266 (1985).

Ellis, V. et al., J. Biol. Chem., 264:2185–88 (1989).

Giannis et al., Adv. In Drug Res. 29:1–78 (1997).

Hansen et al., Biochemistry, 33:4847–64 (1994).

Hruby, V.J., Biopolymers 33:1073–1082 (1993).

Kobayashi, H. et al., Int. J. Cancer, 57:727–33 (1994).

Magdolen et al., Eur. J. Biochem., 237:743–51 (1996).

Moore et al., Adv. In Pharmacol 33:91–141 (1995).

Robbiati et al., Fibrinolysis, 4:53–60 (1990).

Stoppelli et al., Proc. Natl. Acad. Sci. USA 82:4939–43 (1985).

Stratton–Thomas et al., Protein Engineering 8:463–70 (1995).

Wiley, R.A. et al., Med. Res. Rev. 13:327–384 (1993).

* cited by examiner

Primary Examiner—Michael Borin
(74) Attorney, Agent, or Firm—Venable; Shmuel Livnat

(57) ABSTRACT uPAR-targeting cyclic peptide compounds have 11 amino acids that correspond to human uPA(20–30) [SEQ ID NO:2], or are substitution variants at selected positions. The N and C terminal residues of these peptides are joined by a linking group L, so that the linear dimension between the a carbons of the first and the eleventh amino acids is between about 4 and 12 Ångstrom units. These cyclic peptides may be further conjugated to diagnostic labels or therapeutic moieties such as radionuclides. Such compounds are usefull for targeting uPAR expressed in pathological tissues and for inhibiting the binding of uPA to the uPAR. The pharmaceutical and therapeutic compositions inhibit cell migration, cell invasion, cell proliferation or angiogenesis, or induce apoptosis, and are thus useful for treating diseases or condition associated with undesired cell migration, invasion, proliferation, or angiogenesis, most notably cancer. The cyclic peptides are also used to detect and isolate cells expressing uPAR.

60 Claims, 6 Drawing Sheets

Urokinase Plasminogen Activator (uPA)

UNSTIMULATED HMVEC        STIMULATED (bFGF + VEGF) HMVEC

SEQUENCE LISTING

<160> NUMBER OF SEQ ID NOS: 7

<210> SEQ ID NO 1
<211> LENGTH: 411
<212> TYPE: PRT
<213> ORGANISM: Homo sapiens

<400> SEQUENCE: 1

```
Ser Asn Glu Leu His Gln Val Pro Ser Asn Cys Asp Cys Leu Asn Gly
 1               5                  10                  15

Gly Thr Cys Val Ser Asn Lys Tyr Phe Ser Asn Ile His Trp Cys Asn
                20                  25                  30

Cys Pro Lys Lys Phe Gly Gly Gln His Cys Glu Ile Asp Lys Ser Lys
            35                  40                  45

Thr Cys Tyr Glu Gly Asn Gly His Phe Tyr Arg Gly Lys Ala Ser Thr
        50                  55                  60

Asp Thr Met Gly Arg Pro Cys Leu Pro Trp Asn Ser Ala Thr Val Leu
 65                  70                  75                  80

Gln Gln Thr Tyr His Ala His Arg Ser Asp Ala Leu Gln Leu Gly Leu
                85                  90                  95

Gly Lys His Asn Tyr Cys Arg Asn Pro Asp Asn Arg Arg Arg Pro Trp
            100                 105                 110

Cys Tyr Val Gln Val Gly Leu Lys Leu Leu Val Gln Glu Cys Met Val
        115                 120                 125

His Asp Cys Ala Asp Gly Lys Lys Pro Ser Ser Pro Glu Glu Leu
130                 135                 140

Lys Phe Gln Cys Gly Gln Lys Thr Leu Arg Pro Arg Phe Lys Ile Ile
145                 150                 155                 160

Gly Gly Glu Phe Thr Thr Ile Glu Asn Gln Pro Trp Phe Ala Ala Ile
                165                 170                 175

Tyr Arg Arg His Arg Gly Gly Ser Val Thr Tyr Val Cys Gly Gly Ser
            180                 185                 190

Leu Ile Ser Pro Cys Trp Val Ile Ser Ala Thr His Cys Phe Ile Asp
        195                 200                 205

Tyr Pro Lys Lys Glu Asp Tyr Ile Val Tyr Leu Gly Arg Ser Arg Leu
    210                 215                 220

Asn Ser Asn Thr Gln Gly Glu Met Lys Phe Glu Val Glu Asn Leu Ile
225                 230                 235                 240

Leu His Lys Asp Tyr Ser Ala Asp Thr Leu Ala His His Asn Asp Ile
                245                 250                 255

Ala Leu Leu Lys Ile Arg Ser Lys Glu Gly Arg Cys Ala Gln Pro Ser
            260                 265                 270

Arg Thr Ile Gln Thr Ile Cys Leu Pro Ser Met Tyr Asn Asp Pro Gln
        275                 280                 285

Phe Gly Thr Ser Cys Glu Ile Thr Gly Phe Gly Lys Glu Asn Ser Thr
    290                 295                 300

Asp Tyr Leu Tyr Pro Glu Gln Leu Lys Met Thr Val Val Lys Leu Ile
305                 310                 315                 320

Ser His Arg Glu Cys Gln Gln Pro His Tyr Tyr Gly Ser Glu Val Thr
                325                 330                 335

Thr Lys Met Leu Cys Ala Ala Asp Pro Gln Trp Lys Thr Asp Ser Cys
            340                 345                 350

Gln Gly Asp Ser Gly Gly Pro Leu Val Cys Ser Leu Gln Gly Arg Met
```

```
                    355                 360                    365
Thr Leu Thr Gly Ile Val Ser Trp Gly Arg Gly Cys Ala Leu Lys Asp
                370                 375             380
Lys Pro Gly Val Tyr Thr Arg Val Ser His Phe Leu Pro Trp Ile Arg
385                 390                 395                    400
Ser His Thr Lys Glu Glu Asn Gly Leu Ala Leu
                405                 410

<210> SEQ ID NO 2
<211> LENGTH: 11
<212> TYPE: PRT
<213> ORGANISM: Homo sapiens

<400> SEQUENCE: 2

Val Ser Asn Lys Tyr Phe Ser Asn Ile His Trp
1               5                   10

<210> SEQ ID NO 3
<211> LENGTH: 11
<212> TYPE: PRT
<213> ORGANISM: Homo sapiens

<400> SEQUENCE: 3

Val Ser Tyr Lys Tyr Phe Ser Ser Ile Arg Arg
1               5                   10

<210> SEQ ID NO 4
<211> LENGTH: 11
<212> TYPE: PRT
<213> ORGANISM: Homo sapiens

<400> SEQUENCE: 4

Val Ser Tyr Lys Tyr Phe Ser Arg Ile Arg Arg
1               5                   10

<210> SEQ ID NO 5
<211> LENGTH: 11
<212> TYPE: PRT
<213> ORGANISM: Homo sapiens

<400> SEQUENCE: 5

Val Ser Tyr Lys Tyr Phe Ser Arg Ile Gln Arg
1               5                   10

<210> SEQ ID NO 6
<211> LENGTH: 11
<212> TYPE: PRT
<213> ORGANISM: Homo sapiens

<400> SEQUENCE: 6

Met Ser Asn Lys Tyr Phe Ser Ser Ile His Trp
1               5                   10

<210> SEQ ID NO 7
<211> LENGTH: 11
<212> TYPE: PRT
<213> ORGANISM: Homo sapiens

<400> SEQUENCE: 7

Ile Thr Tyr Arg Phe Phe Ser Gln Ile Lys Arg
1               5                   10
```

CYCLIC PEPTIDE LIGANDS THAT TARGET UROKINASE PLASMINOGEN ACTIVATOR RECEPTOR

BACKGROUND OF THE INVENTION

1. Field of the Invention

The present invention relates to cyclic peptides that bind to the cell surface receptor (uPAR) for urokinase plasminogen activator (uPA) and, thus, are capable of delivering therapeutic agents or diagnostic probes to the surfaces of cells expressing this receptor. The invention also relates to pharmaceutical compositions comprising these peptides and their use to inhibit the binding of uPA to its cell surface receptor. By targeting therapeutic agents to uPAR or by inhibiting the binding of uPA to uPAR, it is possible to achieve a number of biological effects that include cell death, the inhibition of cell movement and migration and the inhibition of angiogenesis.

The peptides of the invention are capable of carrying a suitable detectable or imageable label so that they can be used to quantitate uPAR levels in vitro and in vivo. Such compositions are therefore useful as diagnostic, prognostic and imaging tools in all diseases and conditions where this receptor plays a pathological or otherwise undesirable role.

The peptides of the invention can also be immobilized to a suitable matrix and can be used for research applications to identify and isolate cells expressing uPAR and to identify and isolate uPAR from biological samples.

2. Description of the Background Art

The urokinase -type plasminogen activator (uPA) system is strongly linked to pathological processes, such as cell invasion and metastasis in cancer (Danø et al., *Adv. Cancer Res.*, 44:139–266 (1985)). Cells produce uPA in an inactive form, pro-uPA or single-chain uPA (scuPA), which then binds to its receptor, uPAR. This binding event is a prerequisite for the efficient activation of scuPA to two-chain uPA (tcuPA) in a cell milieu (Ellis et al., *J Biol. Chem.*, 264:2185–88 (1989)).

The amino acid sequence of the N-terminus of human pro-uPA [residues 1–44 of SEQ ID NO:1] is Ser Asn Glu Leu His Gln Val Pro Ser Asn Cys Asp Cys Leu Asn Gly 1 10

Gly Thr Cys Val Ser Asn Lys Tyr Phe Ser Asn Ile His Trp Cys Asn Cys 20 30

Pro Lys Lys Phe Gly Gly Gln His Cys Glu Ile 40

The structure of pro-uPA [SEQ ID NO:1] is shown in FIG. 1.

uPA is a three-domain protein comprising (1) an N-terminal epidermal growth factor-like domain, (2) a kringle domain, and (3) a C-terminal serine protease domain. uPAR, the receptor for pro-uPA, is also a multi-domain protein anchored by a glycosylphosphatidylinositol anchor to the outer leaf of the cell membrane (Behrendt et al., *Biol. Chem. Hoppe-Seyler*, 376:269–279 (1995)). The binding of uPA to uPAR initiates two separate events: the first, extracellular proteolysis, is mediated through the activation of plasminogen to plasmin, a broad-spectrum protease which can itself activate matrix metalloprotease (MMP) zymogens (Mazzieri et al., *EMBO J.*, 16: 2319–32 (1997)), release latent growth factors such as TGF-β, IGF-I, and bFGF from their binding proteins or from their binding sites within the extracellular matrix (ECM) (Falcone et al., *J Biol. Chem.*, 268(16): 11951–11958 (1993); Lamarre et al., *Biochem J*, 302: 199–205 (1994); Remacle-Bonnet et al., *Int. J Cancer* 72:835–843 (1997)), and directly remodel certain ECM components such as fibronectin and vitronectin (Wachtfogel et al., *J. Clin. Invest.*, 81:1310–1316 (1988); Sordat et al., *Invasion Metastasis* 14: 223–33 (1994).

The second series of events, triggered by uPA binding to uPAR depends upon transmembrane signal transduction and leads to the stimulation of cell differentiation and motility in several cell types, most notably endothelial cells, epithelial cells and leukocytes (Nusrat et al., *Fibrinolysis* 6 (suppl 1):71–76 (1992); Fazioli et al., *EMBO J.* 16: 7279–86 (1997); Schnaper et al., *J. Cell. Physiol.* 165:107–118 (1994)). This second activity is independent of the proteolytic cascade described above. uPAR mediates these signaling events despite its lack of a transmembrane domain presumably through an adaptor protein(s) which couples extracellular binding to intracellular signaling cascades . The signaling mediated by uPAR probably involves multiple pathways, as with other cytokines. Jak/STAT and MAP-dependent pathways (which overlap with Jak/STAT) have been implicated (Koshelnick et al., *J. Biol. Chem.* 272:28563–28567 (1997); Tang et al., *J. Biol. Chem.* 273:18268–18272 (1998); Dumler et al, *J. Biol. Chem.* 273:315–321 (1998)).

uPAR is not normally expressed at detectable levels on quiescent cells and must therefore be upregulated before it can initiate the activities of the uPA system. uPAR expression is stimulated in vitro by differentiating agents such as phorbol esters (Lund et al., *J. Biol. Chem.* 266:5177–5181 (1991)), by the transformation of epithelial cells, and by various growth factors and cytokines such as VEGF, bFGF, HGF, IL-1, TNFα, (in endothelial cells) and GM-CSF (in macrophages) (Mignatti et al., *J. Cell Biol.* 113:1193–1201 (1991); Mandriota et al., *J. Biol. Chem.* 270:9709–9716; Yoshida et al., *Inflammation* 20:319–326 (1996)). This up-regulation has the functional consequence of increasing cell motility, invasion, and adhesion (Mandriota et al., supra). More importantly, uPAR appears to be up-regulated in vivo in most human carcinomas examined to date, specifically, in the tumor cells themselves, in tumor-associated endothelial cells undergoing angiogenesis and in macrophages (Pyke et al., *Cancer Res.* 53:1911–15 (1993) which may participate in the induction of tumor angiogenesis (Lewis et al., *J. Leukoc. Biol.* 57:747–751 (1995)). uPAR expression in cancer patients is present in advanced disease and has been correlated with a poor prognosis in numerous human carcinomas (Hofinann et al., *Cancer* 78:487–92 (1996); Heiss et al., *Nature Med.* 1:1035–39 (1995). Moreover, uPAR is not expressed uniformly throughout a tumor but tends to be associated with the invasive margin and is considered to represent a phenotypic marker of metastasis in human gastric cancer. The fact that uPAR expression is up-regulated only in pathological states involving ECM remodeling and cell motility such as cancer makes it an attractive marker for diagnosis as well as a selective target for therapy.

In order to design the peptides of the present invention, it was necessary first to identify the minimal binding epitope of uPA for uPAR. It had been shown earlier that the amino terminal fragment of uPA (residues 1–135) that lacked the serine protease domain, sufficed for high affinity (subnanomolar) binding. (Stoppelli et al., *Proc. Natl. Acad. Sci. USA* 82:4939–43 (1985). Subsequent work showed that the growth factor domain alone (residues 1–48) conferred this binding. (Robbiati et al., *Fibrinolysis*, 4:53–60 (1990); Stratton-Thomas et al., *Protein Engineering* 8:463–470 (1995).)

Danø et al., WO 90/12091 (Oct. 18, 1990), disclosed that the binding of uPA to uPAR could be prevented by administering a substance comprising a sequence identical or substantially identical to a uPAR binding site of uPA amino residues 12–32. Rosenberg et al., WO 94/28145(Dec. 9, 1994) disclosed the preparation and use of non-fucosylated HuPA$_{1-48}$ that prevented uPA binding to uPAR.

Earlier studies with peptide fragments within the growth factor domain had shown that residues 20–30 conferred the specificity of binding, but that residues 13–19 were also needed if residues 20–30 were to attain the proper binding conformation. Specifically, the peptide [Ala$^{19}$]uPA(12–32), which contains two cysteines (the third cysteine being replaced by Ala to avoid undesired disulfide bond formations) in its open chain form prevented uPA binding to uPAR with an IC$_{50}$ of 100 nM. In its oxidized cyclic form with an intrachain disulfide bond between Cys$^{13}$ and Cys$^{31}$, the peptide prevented uPA binding with an IC$_{50}$ of 40 nM. The authors proposed that residues 13–19 might act indirectly to provide a scaffold that would help residues 20–30 attain the correct binding conformation (Appella et al., *J. Biol. Chem.*, 262:4437–4440 (1987).

These results were partially confirmed by Kobayashi et al. (*Int. J. Cancer*, 57:727–733 (1994)) who reported that, while the linear peptide 20–30 inhibited the binding of uPA to uPAR with an IC$_{50}$ of 1,000 nM, the longer peptide 17–34 was significantly more potent (IC$_{50}$=100 nM). The corresponding longer peptide (17–34) derived from the mouse sequence inhibited spontaneous metastasis of Lewis Lung carcinoma in mice, whereas the corresponding linear shorter peptide (20–30) did not.

Most recently, Magdolen et al., *Eur. J. Biochem.*, 237:743–751 (1996) reported results of alanine-scanning mutagenesis of the binding loop of the N-terminal uPA fragment and showed that the side chains of Asn22, Lys23, Tyr24, Phe25, Ile28 and Trp30 were important and should be preserved. These authors (citing Hansen et al., *Biochemistry*, 33:4847–64 (1994)), disclosed that the region between Thr18 and Asn32 consisted of a flexible, seven-residue omega loop that is forced into a ring-like structure. In uPA, although Cys19 and Cys31 are in close proximity to each other (0.61 nm), they do not form a disulfide bond with each other. Instead Cys19 bonds with Cys 11, and Cys31 bonds with Cys 13. See FIG. 2. Accordingly, the uPAR binding site of uPA does not form a simple, small ring structure.

In a related, commonly assigned patent application (U.S. Ser. No. 08/47,915, now U.S. Pat. No. 5,542,492 incorporated herein by reference in its entirety) Jones et al. showed that novel cyclic molecules derived from the uPA peptide fragment 20–30 (in which residue 20 is covalently bonded to residue 30) bind to uPAR with IC$_{50}$ values in the 10–100 nM range.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

SUMMARY OF THE INVENTION

The present inventors have discovered cyclic peptides that are useful as diagnostic and therapeutic agents. These peptides are based on the amino acid residues 20–30 (the receptor-binding region) of uPA. However, only six of the 11 amino acid residues in this region are essential for binding: Asn22, Lys23, Tyr24, Phe25, Ile28, and Trp30 (Magdolen et al., supra). The other amino acid residues within the binding region were determined to be non-essential so the peptide can tolerate substitutions with minimal effects on its binding activity. The present inventors have substituted, at these non-essential positions, amino acid residues that may be conjugated to various therapeutic and diagnostic atoms or molecules. Such conjugates would home to sites of uPAR expression, which only occurs in pathological conditions such as cancer. The present inventors have devised linkers to cyclize the linear peptide, providing for economical synthesis and resulting in cyclic peptides that are stable, soluble, bind avidly to uPAR and can serve as carriers of (i) detectable labels for diagnosis and (ii) therapeutic moieties for treatment of a variety of diseases in which uPAR is expressed on pathologic cells or that are treatable by inhibiting the binding of uPA to uPAR.

The therapeutic compositions of the present invention have the ability to (1) kill tumor cells expressing the receptor; (2) promote cell death and inhibit angiogenesis in tumor-associated endothelial cells expressing the receptor; (3) inhibit proteolytic cascades initiated by uPA; (4) inhibit uPA-dependent programmed gene expression; (5) inhibit cell motility, migration, and morphogenesis; (6) inhibit the activation of certain "pro" forms of growth factors to the active form; (7) inhibit angiogenesis; (8) inhibit tumor metastasis; (9) inhibit retinal neovascularization in the treatment of certain forms of blindness; (10) inhibit cell-mediated inflammatory response in diseases such as arthritis; (11) inhibit ischemia; (12) inhibit atheroma formation; and (13) inhibit neointima formation in the process of restenosis.

The present invention is directed to a cyclic peptide compound of the general formula [SEQ ID NO: 2]:

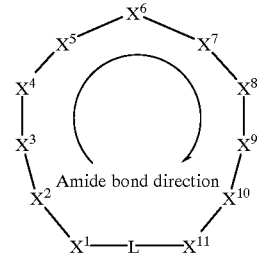

wherein, all of $X^1$ through $X^{11}$ represent D- or L-series amino acids(he binding region). The wild-type human amino acid sequence of $X^1$ through $X^{11}$ is VSNKYFSNIHW [SEQ ID NO:2]. Various positions in $X^1$ through $X^{11}$ may be substituted as follows (with the native human residue indicated first:

$X^1$ is Val, Cys, HomoCys, Glu, Asp, GluR$^1$, AspR$^1$, or Ala;

$X^2$ is Ser, Cys, HomoCys, Glu, Asp, GluR$^1$, AspR$^1$, or Ala;

$X^3$ is Asn or Gln;

$X^4$ is Lys, Arg or His;

$X^5$ is Tyr, Trp, Phe, substituted Phe, di-substituted Phe, HomoPhenylalanine ("HomoPhe"), β-(3-pyridyl) alanine, β-(2-thienyl)alanine, β-(1-naphthyl)-alanine, or β-(2-naphthyl)alanine;

$X^6$ is Phe, Tyr, Trp, substituted Phe, di-substituted Phe, HomoPhe, β-(3-pyridyl)alanine, β-(2-thienyl)alanine, β-(1-naphthyl)alanine, or β-(2-naphthyl)alanine;

$X^7$ is Ser, Cys, HomoCys, Glu, Asp, GluR$^1$, AspR$^1$ or Ala;

$X^8$ is Asn, Cys, HomoCys, Glu, Asp, GluR$^1$, AspR$^1$ or Ala;

$X^9$ is Ile, Leu, Val, NorVal or NorLeu;

$X^{10}$ is His, Cys, HomoCys, Glu, Asp, GluR$^1$, AspR$^1$ or Ala;

$X^{11}$ is Trp, Tyr, Phe, substituted Phe, di-substituted Phe, HomoPhe, β-(3-pyridyl)alanine, β-(2-thienyl)alanine, β-(1-naphthyl)alanine, or β-(2-naphthyl)alanine.

"GluR$^1$" and "AspR$^1$" are substituted glutamic acid and aspartic acid, modified on their γ- and β-COOH groups, respectively, with an R group as described below. "L" or linker groups are described below. When $X^1$–$X^{11}$ is SEQ ID NO:2, then L is not L1 (see below). When $X^1$–$X^{11}$ does contain a Cys, HomoCys, Glu, Asp, GluR$^1$, or AspR$^1$, in the positions indicated above, then L is preferably L1. When linker L includes Cys, HomoCys, Glu, Asp, GluR$^1$ or AspR$^1$ within its structure, then $X^1$, $X^2$, $X^7$, $X^8$ and $X^{10}$ preferably is not Cys, HomoCys, Glu, Asp, GluR$^1$ or AspR$^1$. L is a linking unit or linker, preferably creating a linear dimension between the $C^\alpha$ carbon of amino acid $X^1$ and the $C^\alpha$ carbon of amino acid $X^{11}$ of between about 5 and 10 Ångstrom units, or between about 6 and 8 Ångstrom units.

Reading in the direction $X^1$-L-$X^{11}$, L is preferably of one of the following fourteen basic types, designated L1 through L14:

L1 —CO—CH$_2$—NH—CO—CH$_2$—CH$_2$—CH(CO—NH—CH$_2$—CO—NH$_2$)—NH—

L2 —CO—CH$_2$—NH—CO—CH$_2$—CH$_2$—CH(CO—NH—CH(CH$_2$SH)—CO—NH$_2$)—NH—

L3 —CO—CH(CH$_2$SH)—NH—CO—CH$_2$—CH$_2$—CH(CO—NH—CH$_2$—CONH$_2$)—NH—

L4 —CO—CH$_2$—NH—CO—CH$_2$—CH$_2$—CH(CO—NH—CH(CH$_2$CH$_2$SH)—CO—NH$_2$)—NH—

L5 —CO—CH(CH$_2$CH$_2$SH)—NH—CO—CH$_2$—CH$_2$—CH(CO—NH—CH$_2$—CONH$_2$)—NH—

L6 —CO—CH(CH$_2$CH$_2$COR$^1$)—NH—CO—CH$_2$—CH$_2$—CH(CO—NH—CH$_2$—CONH$_2$)—NH—

L7 —CO—CH(CH$_2$COR$^1$)—NH—CO—CH$_2$—CH$_2$—CH(CO—NH—CH$_2$—CONH$_2$)—NH—

L8 —CO—CH$_2$—NH—CO—CH$_2$—CH$_2$—CH(CO—NH—CH(CH$_2$CH$_2$COR$^1$)—CO—NH$_2$)—NH—

L9 —CO—CH$_2$—NH—CO—CH$_2$—CH$_2$—CH(CO—NH—CH(CH$_2$COR$^1$)—CO—NH$_2$)—NH—

L10 —CO—CH$_2$—NH—CO—CH$_2$—CH$_2$—CH(CO—NH—CH$_2$—COR$^1$)—NH—

L11 —CO—CH(CH$_2$CH$_2$COOH)—NH—CO—CH$_2$—CH$_2$—CH(CO—NH—CH$_2$—CONH$_2$)—NH—

L12 —CO—CH(CH$_2$COOH)—NH—CO—CH$_2$—CH$_2$—CH(CO—NH—CH$_2$—CONH$_2$)—NH—

L13 —CO—CH$_2$—NH—CO—CH$_2$—CH$_2$—CH(CO—NH—CH(CH$_2$CH$_2$COOH)—CO—NH$_2$)—NH—

L14 —CO—CH$_2$—NH—CO—CH$_2$—CH$_2$—CH(CO—NH—CH(CH$_2$COOH)—CO—NH$_2$)—NH—

The R$^1$ group in GluR$^1$, AspR$^1$ and in L6–L10 is —NH—R$^2$—NH$_2$, where the pK$_a$ of each of the primary amino groups in the parent diamine H$_2$N—R$^2$—NH$_2$ is less than about 8.0 and where the pK$_a$ of the primary amino group in —NH—R$^2$—NH$_2$, when it is part R$^1$ is also less than about 8.0. Preferred examples of R$^2$ are p-phenylene, o-phenylene or m-phenylene. It should be recognized that whenever a Cys, HomoCys, Glu, Asp, GluR$^1$ or AspR$^1$ amino acid residue is included in linker L, it may be either the D- or the L- enantiomer.

A most preferred compound has the structure wherein $X^1$–$X^{11}$ is SEQ ID NO:2, L is L10 and R$^1$ is p-phenylenediamine.

In the above compounds, any one of $X^5$, $X^6$ or $X^{11}$ may be mono- or di-substituted Phe, most preferably substituted with halo, a nitro or C1–C6 straight or branched chain alkyl.

The above compounds are characterized by an IC$_{50}$ value in a competitive binding assay to uPAR in vitro of less than about 10$^{-5}$ molar, preferably less than about 10$^{-6}$ molar, most preferably less than about 10$^{-7}$ molar.

Also provided is a uPAR-targeting pharmaceutical composition comprising an effective amount of the cyclic peptide compound as described above and a pharmaceutically acceptable carrier.

Another embodiment is a uPAR-targeting therapeutic composition comprising an effective amount of the cyclic peptide compound described above, to which is bound directly or indirectly a therapeutically active moiety; and a therapeutically acceptable carrier. A preferred therapeutic moiety is a radionuclide, examples of which are $^{125}$I, $^{131}$I, $^{90}$Y, $^{67}$Cu, $^{217}$Bi, $^{211}$At, $^{212}$Pb, $^{47}$Sc, and $^{109}$Pd.

Preferably, the pharmaceutical or therapeutic compositions are in a form suitable for injection.

The compositions of the invention are used in methods and therapeutic compositions to inhibit the binding of uPA to uPAR and to target various therapeutic agents to tissues expressing uPAR, particularly in the treatment of cancer.

Thus, included here is a method for inhibiting cell migration, cell invasion, cell proliferation or angiogenesis, or for inducing apoptosis, comprising contacting cells associated with undesired cell migration, invasion, proliferation or angiogenesis with an effective amount of any of the compositions described above. In a preferred embodiment, the method is used to inhibit the invasiveness of tumor cells.

The present invention also provides a method for treating a subject, preferably a human, having a disease or condition associated with undesired cell migration, invasion, proliferation, or angiogenesis, comprising administering to the subject an effective amount of a pharmaceutical or therapeutic composition as described above.

A nonlimiting list of diseases or conditions treatable as above is given below, and includes as a preferred embodiment, primary growth of solid tumors or leukemias and lymphomas, metastasis, invasion, and/or growth of tumor metastases.

In another embodiment, this invention includes a diagnostically useful uPAR-targeting ligand composition which comprises a cyclic peptide compound described above that is diagnostically labeled, and a diagnostically acceptable carrier. Preferred detectable labels include a radionuclide, a PET-imageable agent, a fluorescer, a fluorogen, a chromophore, a chromogen, a phosphorescer, a chemiluminescer or a bioluminescer. A most preferred radionuclide is selected from the group consisting of $^3$H, $^{14}$C, $^{35}$S, $^{99}$Tc, $^{123}$I, $^{125}$I, $^{131}$I, $^{111}$In, $^{97}$Ru, $^{67}$Ga, $^{68}$Ga, $^{72}$As, $^{89}$Zr and $^{201}$Tl.

In the diagnostic composition, the fluorescer or fluorogen is preferably fluorescein, rhodamine, dansyl, phycoerytlirin, phycocyanin, allophycocyanin, o-phthaldehyde, fluorescamine, a fluorescein derivative, Oregon Green, Rhodamine Green, Rhodol Green or Texas Red.

Also provided is a method for detecting the presence of uPAR (i) on the surface of a cell, (ii) in a tissue, (iii) in an organ or (iv) in a biological sample, which cell, tissue, organ or sample is suspected of expressing uPAR due to a pathological state, comprising:

(a) contacting the cell, tissue, organ or biological sample with the diagnostic composition above and (b) detecting the presence of the label associated with the cell, tissue, organ or sample.

In the above diagnostic method, the contacting may be in vivo and the detecting in vitro. In another embodiment, the contacting and the detecting are both accomplished in vivo.

This invention also includes an affinity ligand useful for binding to or isolating/enriching uPAR, comprising any of the above cyclic peptide compounds immobilized to a solid support or carrier. Such a ligand may be used to isolate uPAR from a complex mixture by (a) contacting the mixture with the affinity ligand; (b) allowing any uPAR to bind to the ligand; (c) removing unbound material from the ligand; and (d) eluting the bound uPAR, thereby isolating or enriching the uPAR.

Also provided is a method for isolating or enriching uPAR-expressing cells from a cell mixture, comprising: (a) contact the cell mixture with the uPAR-binding ligand compound as described above; (b) allowing any uPAR-expressing cell to bind to the compound; (c) separating cells bound to the ligand from unbound cells; and (d) removing the bound cells from the ligand (and optionally separating away the ligand), thereby isolating or enriching the uPAR-expressing cells. In a preferred embodiment such a method utilizes flow cytometric or "fluorescence-activated" cell sorting with a fluorescently labeled cyclic peptide compound.

Alternatively, uPAR-expressing cells are isolated from a cell mixture by (a) contacting the cell mixture with the above affinity ligand; (b) allowing any uPAR-expressing cell to bind to the ligand; (c) removing unbound cells from the ligand and from the bound cells; and (d) releasing the bound cells, thereby isolating or enriching the uPAR-expressing cells.

DESCRIPTION OF THE PREFERRED EMBODIMENTS

Figure 1:
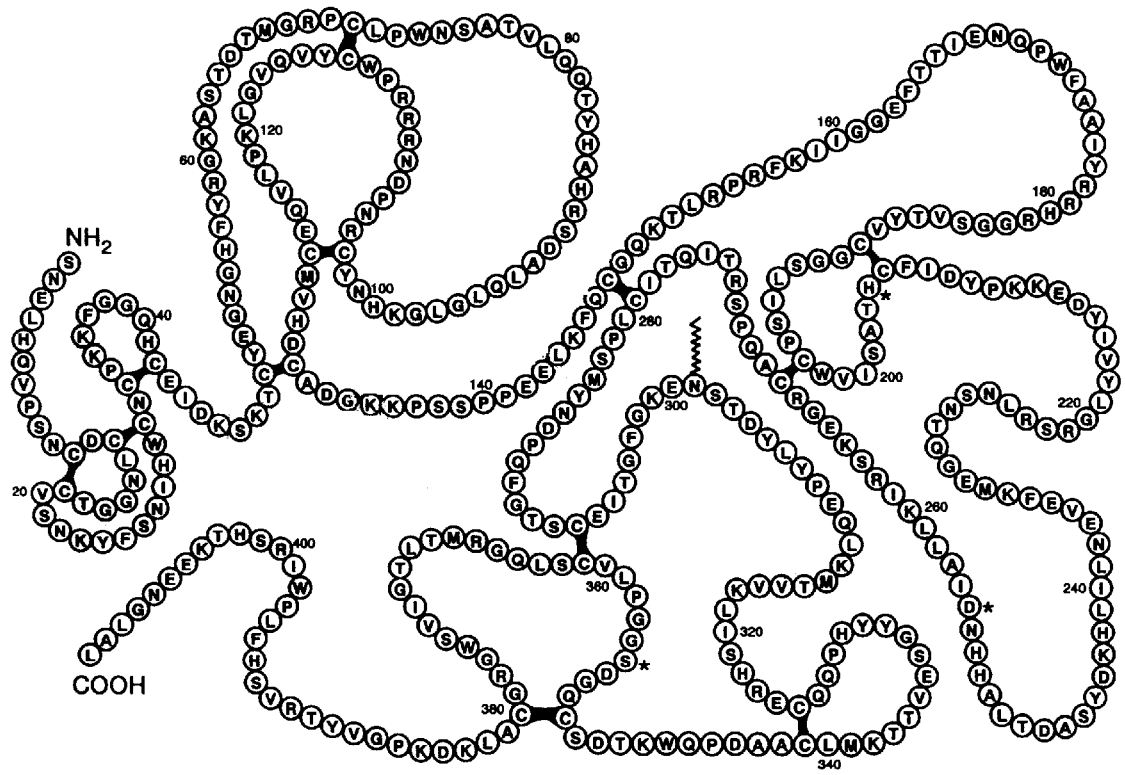
FIG. 1 is a schematic representation of the pro-uPA molecule (SEQ ID NO: 1]
Figure 2:
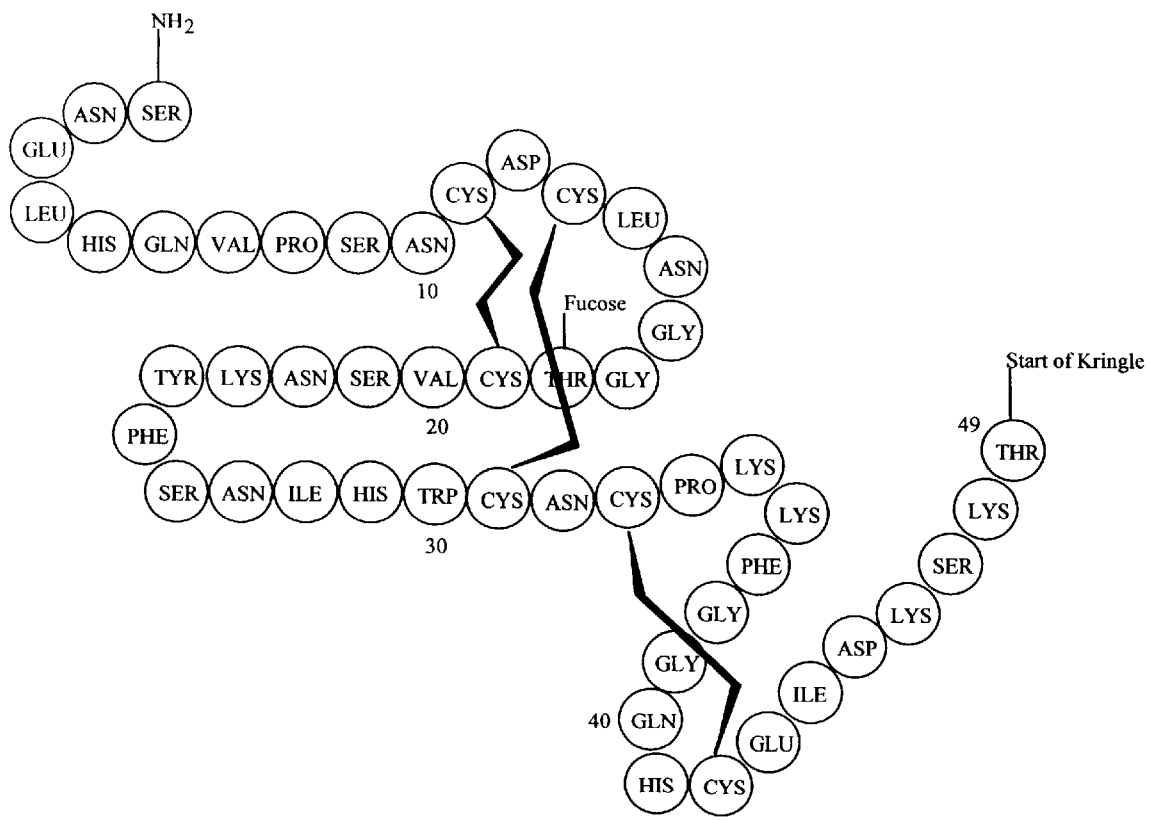
FIG. 2 shows the N-terminal growth factor domain of human uPA.

The present inventors have designed cyclic peptides capable of binding to uPAR, a receptor expressed in pathological conditions such as tumors, which peptides can be modified to incorporate therapeutic moieties without significant alteration in their binding properties. When linked to therapeutic moieties such as toxins and radioactive "warheads," these peptides are used for selective delivery of these moieties to a tumor.

Since these peptides are also antagonists of uPA binding to uPAR, and inhibition of this interaction has been demonstrated to result in decreased metastasis, tumor growth, and angiogenesis, the present inventors conceived that a therapeutic conjugate comprising a uPAR-binding cyclic peptide and, for example, a radiotherapeutic would possess enhanced activity relative to either component alone. The potentiation of anti-angiogenic therapy with radiotherapy for suppressing tumor progression has recently been demonstrated (Mauceri et al., Nature 394:287–91 (1998)). However, in that example, the radiotherapy was not targeted to the tumor but, rather, was administered systemically. A uPAR-targeted radiotherapeutic should have, at minimum, a similar anti-tumor effect, but with less systemic toxicity. The targeted approach described herein allows the administration of lower doses of systemic radioactivity while maintaining the same therapeutic effect, resulting in decreased non-specific exposure to radioactivity.

The present invention provides linkers that were designed to make the cyclic peptides water-soluble and easily synthesizable. Single functional groups were incorporated into the peptides for conjugating to a wide variety of therapeutically and diagnostically useful moieties. The peptides were designed so that modification of these functional groups does not introduce undesirable modifications in the binding region (residues in the peptide corresponding to Asn22, Lys23, Tyr24, Phe25, Ile28 and Trp30 of uPA).

Cys, HomoCys, Glu, Asp, GluR$^1$ or AspR$^1$ residues have been substituted at single, non-essential amino acid position in the 11-mer sequence [SEQ ID NO:2] that comprises the "loop" of the cyclic peptide, specifically at positions 1, 2, 7, 8 and 10 (corresponding to 20, 21, 26, 27, and 29 of uPA). Each peptide has, at most, a single residue replaced by Cys, HomoCys, Glu, Asp, GluR$^1$ or AspR$^1$. In addition, amino acid residues within the linker may also be replaced with Cys, HomoCys, Glu, Asp, GluR$^1$ or AspR$^1$ leaving the 11 amino acids of the binding region intact as in native uPA. These series of peptides may be modified further using any thiol-selective (for Cys-containing peptides), carboxyl-selective (for Glu- and Asp-containing peptides) or amine-selective (for GluR$^1$- and AspR$^1$-containing peptides) reagent.

A weakly basic diamine may be introduced into the linker region via Glu or Asp in peptides containing linkers L11–L14 or into peptides containing Glu or Asp at non-essential positions within the binding region. Such a diamine is not limited by structure, it is required only that the pK$_a$ of each of the amino groups within it is less than about 8.0 even after coupling (as described above). The diamine may be symmetric or non-symmetric. A phenylenediamine, infra, is a simple example of a weakly basic diamine. However, the diamine need not be cyclic. For example a class of non-cyclic diamines are the α,ω-bis-(aminooxy)n-alkanes containing at least two carbon atoms. Another class of suitable non-cyclic diamines is exemplified by the formula NH$_2$CH$_2$CONH(CH$_2$)CN—H—CO—CH$_2$NH$_2$ wherein x>2. A diamine within the scope of this invention may be cyclic and if so, homocyclic or heterocyclic; it may be substituted with one or more substituents drawn from a broad range. A diamine may be polycyclic wherein the various rings may be fused, unfused or even both, and wherein the rings may be homocyclic, heterocyclic or even both; it may be substituted with one or more substituents drawn from a broad range. The amine groups may be direct substituents upon the cycle or spaced therefrom or both. The above examples are non-limiting and are merely illustrative of the broad structural nature allowable to a diamine that may be used within the scope of this invention. Phenylenediamines are chosen as an example, and when introduced into the linker region of a uPAR-targeting peptide of this invention, the phenylenediamine groups can be modified at slightly acidic pH (6.5–7.0) by any amine-reactive reagent without the undesired side effect of modifying the critical Lys residue at position $X^4$ (corresponding to Lys23 in uPA) within the peptide. Peptides modified in this way retain binding activity to whole cells e.g., tumor cells, endothelial cells, tumor tissue sections even after conjugation with Oregon Green (a fluorophore) or with biotin.

The preferred amino acid sequence [SEQ ID NO:2] and the preferred substitutions of the cyclic peptides are as follows:

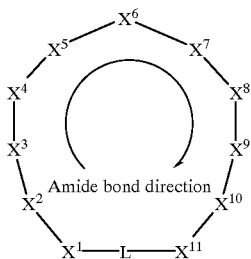

wherein, all of $X^1$ through $X^{11}$ represent D- or L-series amino acids (the binding region). The wild-type human amino acid sequence of $X^1$ through $X^{11}$ in uPA is VSNKYF-SNIHW [SEQ ID NO:2]. Various positions in $X^1$ through $X^{11}$ may be substituted as follows:

$X^1$ is Val, Cys, HomoCys, Glu, Asp, GluR$^1$, AspR$^1$, or Ala;

$X^2$ is Ser, Cys, HomoCys, Glu, Asp, GluR$^1$, AspR$^1$, or Ala;

$X^3$ is Asn or Gln;

$X^4$ is Lys, Arg or His;

$X^5$ is Tyr, Trp, Phe, substituted Phe, di-substituted Phe, HomoPhenylalanine ("HomoPhe"), β-(3-pyridyl)alanine, β-(2-thienyl)alanine, β-(1-naphthyl)alanine, or β-(2-naphthyl)alanine;

$X^6$ is Phe, Tyr, Trp, substituted Phe, di-substituted Phe, HomoPhe, β-(3-pyridyl)alanine, β-(2-thienyl)alanine, β-(1-naphthyl)alanine, or β-(2-naphthyl)alanine;

$X^7$ is Ser, Cys, HomoCys, Glu, Asp, GluR$^1$, AspR$^1$ or Ala;

$X^8$ is Asn, Cys, HomoCys, Glu, Asp, GluR$^1$, AspR$^1$ or Ala;

$X^9$ is Ile, Leu, Val, NorVal or NorLeu;

$X^{10}$ is His, Cys, HomoCys, Glu, Asp, GluR$^1$, AspR$^1$ or Ala;

$X^{11}$ is Trp, Tyr, Phe, substituted Phe, di-substituted Phe, HomoPhe, β-(3-pyridyl)alanine, β-(2-thienyl)alanine, β-(1-naphthyl)alanine, or β-(2-naphthyl)alanine;

When $X^1$–$X^{11}$ is SEQ ID NO:2, then L is not L1. When $X^1$–$X^{11}$ is substituted with one or more of Cys, HomoCys, Glu, Asp, GluR$^1$, or AspR$^1$, then L is preferably L1. GluR$^1$ and AspR$^1$ are substituted glutamic acid and aspartic acid, modified on their γ- and β-COOH groups, respectively, with an R$^1$ group as described below.

The linker moiety L can be of the type designated L1–L14 above and forms a bridge between $X^{11}$ and $X^1$, thus cyclizing the peptide. When the linker L includes Cys, HomoCys, Glu, Asp, GluR$^1$ or AspR$^1$ within its structure, they may be either the D- or L- enantiomers, and $X^1$, $X^2$, $X^7$, $X^8$ and $X^{10}$ preferably are not modifiable residues such as Cys, HomoCys, Glu, Asp, GluR$^1$ or AspR$^1$. In other words, preferably only one modifiable moiety is introduced into each peptide, whether in the $X^1$–$X^{11}$ sequence or within L.

However, in other embodiments, uPAR-targeting cyclic peptides of this invention may include more than one, preferably two, modifiable amino acid sites to accommodate, for example, a cross-linking moiety in one position and a detectable label or a therapeutic moiety in the other.

Furthermore, as stated above, any one of $X^5$, $X^6$ or $X^{11}$ may be a substituted or disubstituted phenylalanine; the substituent may be a halo group, such as 4-fluoro, 4-chloro, 4-bromo, or 3,4-dichloro; a C1–C6 straight or branched chain alkyl; a nitro, or the like.

R$^1$ in GluR$^1$, AspR$^1$ and in linkers L6–L10 is —NH—R$^2$—NH$_2$, such that the pK$_a$ of each of the NH$_2$ groups in the parent diamine, H$_2$N—R$^2$—NH$_2$, is less than about 8.0 and such that the PK$_a$ of the primary amino group in —NH—R$^2$—NH$_2$, when it is in GluR$^1$, AspR$^1$ or the linker, L, is also less than about 8.0. Preferred examples of the R$^2$ group are p-phenylene, o-phenylene or m-phenylene.

The present invention is also directed to the above peptides having an amino acid sequence corresponding to homologues of human uPA in other animal species. Several known animal sequences for residues corresponding to human uPA(20–30), the uPAR binding region, are:

| Human | VSNKYFSNIHW | [SEQ ID NO:2] |
| Rat | VSYKYFSSIRR | [SEQ ID NO:3] |
| Mouse | VSYKYFSRIRR | [SEQ ID NO:4] |
| Pig | VSYKYFSNIQR | [SEQ ID NO:5] |
| Baboon | MSNKYFSSIHW | [SEQ ID NO:6] |
| Chicken | ITYRFFSQIKR | [SEQ ID NO:7] | uPA-uPAR interactions may exhibit varying degrees of species specificity. Thus, it is always preferred to use a cyclic peptide having the amino acid sequence (or a substitution variant thereof) of the species of the cells or animals being targeted or treated.

Based on the foregoing, preferred substituted peptides $X^1$–$X^{11}$ [SEQ ID NO:3] derived from rat uPA are:

$X^1$ is Val, Cys, HomoCys, Glu, Asp, GluR$^1$, AspR$^1$ or Ala;

$X^2$ is Ser, HomoCys, Glu, Asp, GluR$^1$, AspR$^1$ or Ala;

$X^3$ is Tyr, Trp, Phe, substituted Phe, di-substituted Phe, HomoPhe, β-(3-pyridyl)alanine, β-(2-thienyl)alanine, β-(1-naphthyl)alanine, or β-(2-naphthyl)alanine;

$X^4$ is Lys, Arg or His;

$X^5$ is Tyr, Trp, Phe, substituted Phe, di-substituted Phe, HomoPhe, β-(3-pyridyl)alanine, β-(2-thienyl)alanine, β-(1-naphthyl)alanine, or β-(2-naphthyl)alanine;

$X^6$ is Phe, Tyr, Trp, substituted Phe, di-substituted Phe, HomoPhe, β-(3-pyridyl)alanine, β-(2-thienyl)alanine, β-(1-naphthyl)alanine, or β-(2-naphthyl)alanine;

$X^7$ is Ser, Cys, HomoCys, Glu, Asp, GluR$^1$, AspR$^1$ or Ala;

$X^8$ is Ser, Cys, HomoCys, Glu, Asp, GluR$^1$, AspR$^1$ or Ala;

$X^9$ is Ile, Leu, Val, NorVal or NorLeu;

$X^{10}$ is Arg, Cys, HomoCys, Glu, Asp, GluR$^1$, AspR$^1$, Lys, His or Ala;

$X^{11}$ is Arg, Lys or His.

Preferred substituted peptides $X^1$–$X^{11}$ [SEQ ID NO:4] derived from mouse uPA are:

$X^1$ is Val, Cys, HomoCys, Glu, Asp, GluR$^1$, AspR$^1$ or Ala;

$X^2$ is Ser, Cys, HomoCys, Glu, Asp, GluR$^1$, AspR$^1$ or Ala;

$X^3$ is Tyr, Trp, Phe, substituted Phe, di-substituted Phe, HomoPhe, β-(3-pyridyl)alanine, β-(2-thienyl)alanine, β-(1-naphthyl)alanine, or β-(2-naphthyl)alanine;

$X^4$ is Lys, Arg or His;

$X^5$ is Tyr, Trp, Phe, substituted Phe, di-substituted Phe, HomoPhe, β-(3-pyridyl)alanine, β-(2-thienyl)alanine, β-(1-naphthyl)alanine, or β-(2-naphthyl)alanine;

$X^6$ is Phe, Tyr, Trp, substituted Phe, di-substituted Phe, HomoPhe, β-(3-pyridyl)alanine, β-(2-thienyl)alanine, β-(1-naphthyl)alanine, or β-(2-naphthyl)alanine;

$X^7$ is Ser, Cys, HomoCys, Glu, Asp, $GluR^1$, $AspR^1$ or Ala;

$X^8$ is Arg, Cys, HomoCys, Glu, Asp, $GluR^1$, $AspR^1$, Lys, His or Ala;

$X^9$ is Ile, Leu, Val, NorVal or NorLeu;

$X^{10}$ is Arg, Cys, HomoCys, Glu, Asp, $GluR^1$, $AspR^1$, Lys, His or Ala;

$X^{11}$ is Arg, Lys or His

It will be clear to one skilled in the art that similar substitutions can be made in the peptides corresponding to the uPAR binding fragment of uPA of other animal species in keeping with the teachings set forth above.

Cyclic Peptides

In the general formula, above, the amide bond (CO—NH) linking $X^1$ to $X^2$, is such that the carbonyl moiety is from amino acid $X^1$ and the amino moiety is from the amino acid $X^2$. The same is true for the link between $X^2$ and $X^3$, and so on within the 11mer peptide. The peptide has $X^1$ as its N-terminus and $X^{11}$ as its C-terminus.

To prepare a compound of Formula 1, L is chosen to provide, at one terminus, a functional group that can be chemically bonded to the carboxyl C atom of amino acid $X^{11}$ and, at the other terminus, a functional group that can be chemically bonded to the α-amino N atom of amino acid $X^1$.

It is preferred that the linker L confer water solubility to the peptide and result in an intramolecular distance of 4–12 Å between the Cα of the N-terminal residue $X^1$ and the Cα of the C-terminal residue $X^{11}$.

Alternatively, the linear peptide $X^1$-$X^2$-$X^3$-$X^4$-$X^5$-$X^6$-$X^7$-$X^8$-$X^9$-$X^{10}$-$X^{11}$ can be synthesized with an extension at $X^{11}$ comprising a portion of the ultimate final linker group L; that extension is termed $L_b$. After synthesis of the peptide chain, the $X^1$ terminus is extended with an extension that will also become part of the ultimate linker; this group is designated $L_a$. These steps yield a compound of the formula:

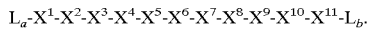

$L_a$-$X^1$-$X^2$-$X^3$-$X^4$-$X^5$-$X^6$-$X^7$-$X^8$-$X^9$-$X^{10}$-$X^{11}$-$L_b$.

The free ends of $L_a$ and $L_b$ are then chemically bonded to each other. In this way, the linker L is formed during the cyclization step from pre-attached fragments $L_a$ and $L_b$. In the examples given below for L, the direction of L, reading left to right, is from to $X^1$ to $X^{11}$, ie., the C-terminus of L is bonded to $X^1$, and the N-terminus of L is bonded to $X^{11}$.

When L includes a Cys, HomoCys, Glu, Asp, γ-carboxyl modified Glu or a β-carboxyl modified Asp residue, the configuration of the enantiomeric center of such a residue can be either L- or D-.

Cyclic peptides having a $GluR^1$ or $AspR^1$ residue within $X^1$–$X^{11}$ $GluR^1$ and $AspR^1$ may be incorporated directly into the peptides of the invention during synthesis. Glu and Asp in which the α-carboxyl group has been protected may be modified using any diamine $NH_2$—$R^2$—$NH_2$. The newly incorporated —$NH_2$ group is then blocked with a fluorenylmethyloxycarbonyl (FMOC) group. Alternatively, the diamine $NH_2$-$R^2$—$NH_2$ may be blocked first to provide $NH_2$—$R^2$—NH—FMOC which is then coupled to the side chain carboxyl of the Asp or Glu in which the α-carboxyl group has been protected. Howsoever obtained, the modified amino acid is incorporated into the cyclic peptides of the invention using standard peptide synthetic techniques as described below.

Cyclic Peptides having an L6, L7, L8, L9 or L10-type Linker

To prepare the compounds having a linker L of the L6, L7, L8, L9 or L10 type, the L is chosen to provide, at one terminus, a functional group that can be chemically bonded to the carboxyl C atom of amino acid $X^{11}$ and, at the other terminus, a functional group that can be chemically bonded to the α-amino N atom of amino acid $X^1$.

It is preferred that linker L confer water solubility to the peptide and result in an interatomic distance of 4–12 Å between the Cα of the N-terminal residue $X^1$ and the Cα of the C-terminal residue $X^{11}$.

The $R^1$-group may be introduced into the linker L in two different ways (see below):

(a) as part of the peptide synthesis on the resin, or;

(b) by making a peptide intermediate with a linker L containing COOH in lieu of $COR^1$, which intermediate is subsequently modified to incorporate the $R^1$ group.

General Chemical Synthetic Procedures

The peptides of the invention are preferably prepared using solid-phase synthesis, such as that generally described by Merrifield, *J. Amer. Chem. Soc.*, 85:2149–54 (1963), although other equivalent chemical syntheses known in the art are also useful. Solid-phase peptide synthesis may be initiated from the C-terminus of the peptide by coupling a protected α-amino acid to a suitable resin. Such a starting material can be prepared by attaching an α-amino-protected amino acid by an ester linkage to a chloromethylated resin or to a hydroxymethyl resin, or by an amide bond to a BHA resin or MBHA resin.

The preparation of the hydroxymethyl resin is described by Bodansky et al., *Chem. Ind.*, 38:1597–1598 (1966). Chloromethylated resins are commercially available from BioRad Laboratories, Richmond, Calif. and from Lab. Systems, Inc. The preparation of such a resin is described by Stewart et al. ("Solid Phase Peptide Synthesis," Freeman & Co., San Francisco 1969, chapter 1, 1–6). BHA and MBHA resin supports are commercially available and are generally used only when the desired polypeptide being synthesized has an unsubstituted amide at the C-terminus.

The amino acids $X^1$ through $X^{11}$ can be coupled to the growing peptide chain using techniques well known in the art for the formation of peptide bonds. For example, one method involves converting the amino acid to a derivative that will render the carboxyl group of the amino acid more susceptible to reaction with the free N-terminal amino group of the growing peptide chain. Specifically, the C-terminal of the protected amino acid can be converted to a mixed anhydride by the reaction of the C-terminal with ethyl chloroformate, phenyl chloroformate, sec-butyl chloroformate, isobutyl chloroformate, or pivaloyl chloride or the like acid chlorides. Alternatively, the C-terminal of the amino acid can be converted to an active ester, such as a 2,4,5-trichlorophenyl ester, a pentachlorophenyl ester, a pentafluorophenyl ester, a p-nitrophenyl ester, a N-hydroxysuccinimide ester, or an ester formed from 1-hydroxybenzotriazole.

Another coupling method involves the use of a suitable coupling agent, such as N,N'dicyclohexylcarbodiimide or N,N'-diisopropylcarbodiimide. Other appropriate coupling agents, apparent to those skilled in the art, are disclosed in Gross et al., *The Peptides: Analysis, Structure, Biology, Vol. I*, "Major Methods of Peptide Bond Formation," Academic Press, 1979, the disclosure of which is hereby incorporated by reference.

It will be recognized that the a-amino group of each amino acid employed in the peptide synthesis must be protected during the coupling reaction to prevent side reactions involving their active α-amino function. It should also be recognized that certain amino acids contain reactive side-chain functional groups (e.g., sulfhydryl, amino, carboxyl, and hydroxyl) and that such functional groups must also be protected with suitable protecting groups to prevent a chemical reaction from occurring at either (1) the α-amino group site or (2) a reactive side chain site during both the initial and subsequent coupling steps.

In the selection of a particular protecting group to be used in synthesizing the peptides, the following general rules are typically followed. Specifically, an α-amino protecting group (a) should render the α-amino function inert under the conditions employed in the coupling reaction, (b) should be readily removable after the coupling reaction under conditions that will not remove side-chain protecting groups and will not alter the structure of the peptide fragment, and (c) should substantially reduce the possibility of racemization upon activation, immediately prior to coupling.

On the other hand, a side-chain protecting group (a) should render the side chain functional group inert under the conditions employed in the coupling reaction, (b) should be stable under the conditions employed in removing the α-amino protecting group, and (c) should be readily removable from the desired fully-assembled peptide under reaction conditions that will not alter the structure of the peptide chain.

It will be apparent to those skilled in the art that the protecting groups known to be useful for peptide synthesis will vary in reactivity with the agents employed for their removal. For example, certain protecting groups, such as triphenylmethyl and 2-(p-biphenyl)isopropyloxycarbonyl, are very labile and can be cleaved under mild acid conditions. Other protecting groups, such as t-butyloxycarbonyl (BOC), t-amyloxycarbonyl, adamantyl-oxycarbonyl, and p-methoxybenzyloxycarbonyl, are less labile and require moderately strong acids for their removal, such as trifluoroacetic, hydrochloric, or boron trifluoride in acetic acid. Still other protecting groups, such as benzyloxycarbonyl (CBZ or Z), halobenzyloxycarbonyl, p-nitrobenzyloxycarbonyl cycloalkyloxycarbonyl, and isopropyloxycarbonyl, are even less labile and require even stronger acids, such as hydrogen fluoride, hydrogen bromide, or boron trifluoroacetate in trifluoroacetic acid, for their removal. Suitable protecting groups, known in the art are described in Gross et al., *The Peptides: Analysis, Structure, Biology, Vol. 3*: "Protection of Functional Groups in Peptide Synthesis," Academic Press, 1981.

Preferred classes of amino acid protecting groups useful for protecting the α-amino group or for protecting a side chain group are described below.

(1) For an α-amino group, three typical classes of protecting groups are: (a) aromatic urethane-type protecting groups, such as fluorenylmethyloxycarbonyl (FMOC), CBZ, and substituted CBZ, such as, e.g., p-chlorobenzyloxycarbonyl, p-nitrobenzyloxycarbonyl, p-bromobenzyloxycarbonyl, and p-methoxybenzyloxycarbonyl, o-chlorobenzyloxycarbonyl, 2,4-dichlorobenzyloxycarbonyl, 2,6-dichlorobenzyloxycarbonyl, and the like; (b) aliphatic urethane-type protecting groups, such as BOC, t-amyloxycarbonyl, isopropyloxycarbonyl, 2-(p-biphenyl)-isopropyloxycarbonyl, allyloxycarbonyl and the like; and (c) cycloalkyl urethane-type protecting groups, such as cyclopentyloxycarbonyl, adamantyloxycarbonyl, and cyclohexyloxycarbonyl. The preferred α-amino protecting groups are BOC and FMOC.

(2) For the ε-amino group of Lys, protection is attained using any of the groups mentioned above in (1) such as BOC, FMOC, 2-chlorobenzyloxycarbonyl and the like.

(3) For the guanidino group of Arg, protection is attained by nitro, tosyl, CBZ, adamantyloxycarbonyl, 2,2,5,7,8-pentamethylchroman-6-sulfonyl, 2,3,6-trimethyl-4-methoxyphenylsulfonyl, or BOC groups.

(4) For the hydroxyl group of Ser, Thr, or Tyr, protection may be attained by t-butyl; benzyl (BZL); or substituted BZL, such as p-methoxybenzyl, p-nitrobenzyl, p-chlorobenzyl, o-chlorobenzyl, and 2,6-dichlorobenzyl.

(5) For the carboxyl group of Asp or Glu, protection is attained by esterification using such groups as BZL, t-butyl, cyclohexyl, cyclopentyl, and the like. The fluorenylmethyl group can also be also usefully employed.

(6) For the imidazole nitrogen of His, the benzyloxymethyl (BOM), the tosyl, or the 2,4-dinitrophenyl group is suitably employed as a protecting group.

(7) For the phenolic hydroxyl group of Tyr, a protecting group such as tetrahydropyranyl, tert-butyl, trityl, BZL, chlorobenzyl, 4-bromobenzyl, and 2,6-dichlorobenzyl is employed, most preferably bromobenzyloxycarbonyl.

(8) For the amino groups of Asn or Gln, xanthyl (Xan) is preferably employed.

(9) The amino acid Met is preferably left unprotected.

(10) For the thio group of Cys, p-methoxybenzyl can be employed. The acetamidomethyl (Acm) can also be also usefully employed.

(11) For the thio group of HomoCys, p-methoxybenzyl can be employed. The acetamidomethyl (Acm) can also be also usefully employed.

The first C-terminal amino acid of the growing peptide chain, e.g., Lys, is typically protected at the N-amino position by an appropriately selected protecting group such as BOC. The BOC-Lys-(2-chlorobenzyloxycarbonyl)—OH group can be first coupled to a benzylhydrylamine resin using isopropylcarbodiimide at about 25° C. for two hours with stirring or to a chloromethylated resin according to the procedure set forth in Horiki et al., *Chemistry Letters*, 165–168 (1978). Following the coupling of the BOC-protected amino acid to the resin support, the α-amino protecting group is usually removed, typically by using trifluoroacetic acid (TFA) in methylene chloride or TFA alone. The α-amino group de-protection reaction can occur over a wide range of temperatures, but is usually carried out at a temperature between about 0° C. and room temperature.

Other standard α-amino group de-protecting reagents, such as HCl in dioxane, and conditions for the removal of specific α-amino protecting groups are well-known in the art, e.g.,, Luibke et al., *Chemie und Biochemie der Aminosaüren, Peptide und Proteine I*, Chapter II-1, 102–117 (Georg Thieme Verlag Stuttgart 1975), which is hereby incorporated by reference in its entirety. Following the removal of the α-amino protecting group, the unprotected α-amino group (with any side-chain still protected), can be coupled in a stepwise manner in the intended sequence.

An alternative to the stepwise approach is the fragment condensation method in which pre-formed peptides of shorter length, each representing part of the desired sequence, are coupled to a growing chain of amino acids bound to a solid phase support. For this stepwise approach, a particularly suitable coupling reagent is N,N'-dicyclohexyl-carbodiimide or diisopropylcarbodiimide. The selection of the coupling reagent, as well as the choice of the fragmentation pattern needed to couple fragments of the desired nature and size are important for success and are known to those skilled in the art.

Each protected amino acid or peptide is usually introduced into the solid-phase reactor in amounts in excess of stoichiometric quantities, and the coupling is carried out in an organic solvent, such as dimethylformamide (DMF), $CH_2Cl_2$ or mixtures thereof If incomplete coupling occurs, the coupling procedure is customarily repeated before removal of the α-amino protecting group in preparation for coupling to the next amino acid. Following the removal of the α-amino protecting group, the remaining α-amino-protected and side-chain-protected amino acids can be coupled in a stepwise manner in the intended sequence. The success of the coupling reaction at each stage of the synthesis may be monitored. A preferred method of monitoring the synthesis is by the ninhydrin reaction (Kaiser et al., *Anal. Biochem.*, 34:595 (1970)). The coupling reactions can also be performed automatically using well-known commercial methods and devices, for example, a Beckman 990 Peptide Synthesizer.

After it has been synthesized, the protected peptide must be cleaved from the resin support, and all protecting groups must be removed. The cleavage reaction and removal of the protecting groups are suitably accomplished concomitantly or consecutively with de-protection reactions. When the peptide is anchored to the resin by an ester bond, it can be cleaved by any reagent that is capable of breaking an ester linkage and of penetrating the resin matrix. One especially useful method is by treatment with liquid anhydrous hydrogen fluoride. This reagent will usually cleave not only the peptide from the resin, but will also remove all acid-labile protecting groups and, thus, will result in a fully de-protected peptide. When additional acid-stable protecting groups are present, additional de-protection steps must be carried out, either before or after the hydrogen fluoride treatment described above, according to specific needs and circumstances.

When a chloromethylated resin is used, the hydrogen fluoride cleavage/de-protection treatment generally results in the formation of the free peptide acids. When a benzhydrylamine resin is used, the hydrogen fluoride treatment generally results in free peptide amides. Reaction with hydrogen fluoride in the presence of anisole and dimethylsulfide at 0° C. for one hour will typically remove the side-chain protecting groups and, concomitantly, release the peptide from the resin.

In appropriate circumstances and when certain structural requirements of the peptide are met, when it is desired to cleave the peptide without removing protecting groups, the protected peptide-resin can be subjected to methanolysis, thus yielding a protected peptide with a methylated C-terminal carboxyl group. This methyl ester can be hydrolyzed under mild alkaline conditions to give the free carboxyl group. Protecting groups on the peptide chain can then be removed by treatment with a strong acid, such as liquid hydrogen fluoride. A particularly useful technique for methanolysis is that of Moore et al., in *Peptides, Proc. Fifth Amer. Pept. Symp.*, 518–521 (Goodman et al., eds., 1977), which calls for treating the protected peptide-resin with methanol and potassium cyanide in the presence of a crown ether.

Other methods for cleaving a protected peptide from chloromethylated resins include (1) ammonolysis and (2) hydrazinolysis. If desired, the resulting C-terminal amide or hydrazide can be hydrolyzed to the free C-terminal carboxyl moiety, and the protecting groups can be removed conventionally. The protecting group present on the N-terminal α-amino group may be removed either before or after cleaving the protected peptide from the support.

Purification of the cyclic peptides of the invention is typically achieved using chromatographic techniques, such as preparative HPLC (including reverse phase HPLC), and other forms of chromatography including gel permeation, ion exchange, partition and affinity. Preferred affinity matrices comprise antibodies, preferably monoclonal antibodies). Other purification approaches include conventional techniques such as countercurrent distribution and the like.

Incorporation of $R^1$ groups into Peptides containing Glu or Asp

The $R^1$ group may be incorporated into the peptides of the invention after synthesis and purification of the peptides. Peptides containing Glu or Asp in $X^1$–$X^{11}$ or peptides containing linkers L11–L14 may be modified by reaction with $HR^1$, where $R^1$ is —NH—$R^2$—$NH_2$. $HR^1$ is preferably a phenylenediamine and may be incorporated via the γ- or β-carboxyl side chains of Glu and Asp, respectively, using a water soluble carbodiimide such as 1-ethyl-3-(3-dimethylaminopropyl)carbodiimide (EDC).

Peptidomimetics

A preferred type of chemical derivative of the peptides described herein is a peptidomimetic compound which mimics the biological effects of the Compositions. A peptidomimetic agent may be an unnatural peptide or a non-peptide agent which recreates the stereospatial properties of the binding elements of the Compositions such that it has the binding activity or biological activity of the Compositions. Similar to the cyclic peptides of the Compositions, a peptidomimetic will have a binding face (which interacts with uPAR) and a non-binding face. Again, similar to the cyclic peptides of the Compositions, the non-binding face of a peptidomimetic will contain functional groups which can be modified by various therapeutic and diagnostic moieties without modifying the binding face of the peptidomimetic. A preferred embodiment of a peptidomimetic would contain an aniline on the non-binding face of the molecule. The $NH_2$-group of an aniline has a pKa~4.5 and could therefore be modified by any $NH_2$-selective reagent without modifying any $NH_2$ functional groups on the binding face of the peptidomimetic. Other peptidomimetics may not have any $NH_2$ functional groups on their binding face and therefore, any $NH_2$, without regard for $pK_a$ could be displayed on the non-binding face as a site for conjugation. In addition other modifiable functional groups, such as —SH and —COOH could be incorporated into the non-binding face of a peptidomimetic as a site of conjugation. A therapeutic or diagnostic moiety could also be directly incorporated during the synthesis of a peptidomimetic and preferentially be displayed on the non-binding face of the molecule.

This invention also includes compounds which retain partial peptide characteristics. For example, any proteolytically unstable bond within a cyclic peptide of the invention could be selectively replaced by a non-peptidic element such as an isostere (N-methylation; D-amino acid at the $S_1$ site) or a reduced peptide bond while the rest of the molecule retains its peptide nature.

Peptidomimetic compounds, either agonists, substrates or inhibitors, have been described for a number of bioactive peptides such as opioid peptides, VIP, thrombin, HIV protease, etc. Methods for designing and preparing peptidomimetic compounds are known in the art (Hruby, V. J., *Biopolymers* 33:1073–1082 (1993); Wiley, R. A. et al., *Med. Res. Rev.* 13:327–384 (1993); Moore et al., *Adv. in Pharmacol* 33:91–141 (1995); Giannis et al., *Adv. in Drug Res.* 29:1–78 (1997), which references are incorporated by reference in their entirety). These methods are used to make peptidomimetics that possess at least the binding capacity and specificity of the cyclic peptides and preferably also possess the biological activity. Knowledge of peptide chemistry and general organic chemistry available to those skilled in the art are sufficient, in view of the present disclosure, for designing and synthesizing such compounds.

For example, such peptidomimetics may be identified by inspection of the cystallographically-derived three-dimensional structure of a peptide of the invention either free or bound in complex with uPAR. Alternatively, the structure of a peptide of the invention bound to uPAR can be gained by the techniques of nuclear magnetic resonance spectroscopy. The better knowledge of the stereochemistry of the interaction of a cyclic peptide with its receptor will permit the rational design of such peptidomimetic agents.

All the foregoing peptides, as well as their variants and chemical derivatives, including peptidomimetics, must bind to human uPAR with an $IC_{50} \leq 10$ $\mu$M. This activity is characterized in greater detail below.

In Vitro Testing of Compositions

A. Assay for ligand binding to uPAR on whole cells

The uPAR-targeting ligand compounds of the invention are readily tested for their binding to uPAR, preferably by measuring their ability to inhibit the binding of $[^{125}I]$DFP-uPA to uPAR in a competitive ligand-binding assay. The assay may employ whole cells that express uPAR, for example cells lines such as RKO or HeLa. A preferred assay is conducted as follows. Cells (about $5 \times 10^4$/well) are plated in medium (e.g., MEM with Earle's salts/10% FBS+ antibiotics) in 24-well plates, then incubated in a humid 5% $CO_2$ atmosphere until the cells reach 70% confluence. Catalytically inactivated high molecular weight uPA (DFP-uPA) is radioiodinated using Iodo-gen® (Pierce) to a specific activity of about 250,000 cpm/mg. The cell-containing plates are then chilled on ice and the cells are washed twice (5 minutes each) with cold PBS/0.05% Tween-80. Test compounds are serially diluted in cold PBS/0.1% BSA/0.01% Tween-80 and added to each well to a final volume of 0.3 mL 10 minutes prior to the addition of the $[^{125}I]$DFP-uPA. Each well then receives 9500 cpm of $[^{125}I]$DFP-uPA at a final concentration of 0.2 nM). The plates are then incubated at 4° C. for 2 hrs, after which time the cells are washed 3×(5 minutes each) with cold PBS/0.05% Tween-80. NaOH (1N) is added to each well in 0.5 mL to lyse the cells, and the plate is incubated for 5 minutes at room temperature or until all the cells in each well are lysed as determined by microscopic examination. The contents of each well are then aspirated and the total counts in each well determined using a gamma counter. Each compound is tested in triplicate and the results are expressed as a percentage of the total radioactivity measured in wells containing $[^{125}I]$DFP-uPA alone, which is taken to represent maximum (100%) binding.

The inhibition of binding of $[^{125}I]$DFP-uPA to uPAR is usually dose-related, such that the concentration of the test compound necessary to produce a 50% inhibition of binding (the $IC_{50}$ value), which is expected to fall in the linear part of the curve, is easily determined. In general, the compounds of the invention have $IC_{50}$ values of less than about $10^{-5}$M. Preferably, the compounds of the invention have $IC_{50}$ values of less than about $10^{-6}$M and, even more preferably, less than about $10^{-7}$M.

B. Assay for the invasion of PC-3 cells

The ability of PC-3 (human prostatic carcinoma) cells to invade through a reconstituted basement membrane (Matrigel®) is measured using transwell tissue culture inserts. Invasive cells are defined as cells which are able to traverse through the Matrigel® and upper aspect of a polycarbonate membrane and adhere to the bottom of the membrane. Transwells (Costar) containing polycarbonate membranes (8.0 $\mu$m pore size) are coated with Matrigel® (Collaborative Research), which has been diluted in sterile PBS to a final concentration of 75 $\mu$g/mL (60 $\mu$L of diluted Matrigel® per insert), and placed in the wells of a 24-well plate. The membranes are dried overnight in a biological safety cabinet, then rehydrated by adding 100 $\mu$L of DMEM containing antibiotics for 1 hour on a shaker table. The DMEM is removed from each insert by aspiration and 0.8 mL of DMEM/10% FBS/antibiotics is added to each well of the 24-well plate such that it surrounds the outside of the transwell ("lower chamber"). Fresh DMEM/antibiotics (100 $\mu$L), human Glu-plasminogen (5 $\mu$g/mL), and any inhibitors to be tested are added to the top, inside of the transwell ("upper chamber"). The tumor cells which are to be tested are trypsinized and resuspended in DMEM/antibiotics, then added to the top chamber of the transwell at a final concentration of 800,000 cells/mL. The final volume of the upper chamber is adjusted to 200 $\mu$L. The assembled plate is then incubated in a humid 5% $CO_2$ atmosphere for 72 hours. After incubation, the cells are fixed and stained using DiffQuik® (Giemsa stain) and the upper chamber is then scraped using a cotton swab to remove the Matrigel® and any cells which did not invade through the membrane. The membranes are detached from the transwell using an X-acto® blade, mounted on slides using Permount® and cover-slips, then counted under a high-powered (400×) field. An average of the cells invaded is determined from 5–10 fields counted and plotted as a function of inhibitor concentration.

C. Assay for endothelial cell migration

Transwells (Costar, 8.0 $\mu$m pore size; for additional description, see Tumor Cell Invasion Methods) are coated with type I collagen (50 $\mu$g/hl) by adding 200 $\mu$L of the collagen solution per transwell, then incubating overnight at 37° C. The transwells are assembled in a 24-well plate and a chemoattractant (e.g., FGF-2) is added to the bottom chamber in a total volume of 0.8 mL media. Endothelial cells, which have been detached from monolayer culture using trypsin, are diluted to a final concentration of $1 \times 10^6$ cells/mL with serum-free media and 0.2 mL of this cell suspension is added to the upper chamber of each transwell. Inhibitors to be tested are added to both the upper and lower chambers, and the migration is allowed to proceed for 5 hrs in a humidified atmosphere at 37° C. The transwells are removed from the plate stained using DiffQuik®. Cells which did not migrate are removed from the upper chamber by scraping with a cotton swab and the membranes are detached, mounted on slides, and counted under a high-power field (400×) to determine the number of cells migrated.

D. Assays for cell proliferation/cytotoxicity

The anti-proliferative and cytotoxic effects of the compositions may be determined for various cell types including tumor cells, endothelial cells, fibroblast, and macrophages. This is especially useful when testing a compound of the invention which has been conjugated to a therapeutic moiety such as a radiotherapeutic or a toxin. For example, a conjugate of one of the compositions with Bolton-Hunter reagent which has been iodinated with $^{131}$I would be expected to inhibit the proliferation of cells expressing uPAR (most likely by inducing apoptosis). These assays are also useful for estimating toxic effects against normal cells, which do not express uPAR. Anti-proliferative effects would be expected against tumor cells and stimulated endothelial cells but not quiescent endothelial cells (see FIG. 6) or normal human dermal fibroblasts, neither of which express uPAR. Any anti-proliferative or cytotoxic effects observed in the normal cells would represent non-specific toxicity of the conjugate.

A typical assay would involve plating cells at a density of 5–10,000 cells per well in a 96-well plate. The conjugate to be tested is added at a concentration 10× the $IC_{50}$ measured in a binding assay (this will vary depending on the conjugate) and allowed to incubate with the cells for 30 minutes. The cells are washed 3X with media, then fresh media containing [$^3$H]thymidine (1 $\mu$Ci/mL) is added to the cells and they are allowed to incubate at 37° C. in 5% $CO_2$ for 24 and 48 hours. Cells are lysed at the various time points using 1M NaOH and counts per well determined using a $\beta$-counter. Proliferation may be measured non-radioactively using MTS reagent or CyQuant® to measure total cell number. For cytotoxicity assays (measuring cell lysis), a Promega 96-well cytotoxicity kit is used. If there is evidence of anti-proliferative activity, induction of apoptosis may be measured using TumorTACS (Genzyme).

In Vivo Study of the uPAR-Targeted Cyclic Peptides

A. Corneal Angiogenesis Model

The protocol used is essentially identical to that described by Volpert et al. (*J. Clin. Invest.* 98:671–679 (1996)). Briefly, female Fischer rats (120–140 gms) are anesthetized and pellets (5 $\mu$l) comprised of Hydron®, bFGF (150 nM), and the compounds to be tested are implanted into tiny incisions made in the cornea 1.0–1.5 mm from the limbus. Neovascularization is assessed at 5 and 7 days after implantation. On day 7, animals are anesthetized and infused with a dye such as colloidal carbon to stain the vessels. The animals are then euthanized, the corneas fixed with formalin, and the corneas flattened and photographed to assess the degree of neovascularization. Neovessels may be quantitated by imaging the total vessel area or length or simply by counting vessels.

B. Matrigel® Plug Assay

This assay is performed essentially as described by Passaniti et al. (*Lab Invest.* 67:519–528 (1992)). Matrigel® is maintained at 4° C. until use. Just prior to injection, Matrigel® is mixed with angiogenic factors (100 ng/mL bFGF, 100 ng/mL VEGF), then injected s.c. into mice (0.5 mL per mouse). The injected Matrigel® forms a palpable solid gel which persists for 10 days, at which time the animals are euthanized. The Matrigel® plugs are removed and angiogenesis quantitated by measuring the amount of hemoglobin in the Matrigel® plugs or by counting neovessels in sections prepared from the plugs. Anti-CD31 staining may be used to confirm neovessel formation and microvessel density in the plugs.

C. Chick chorioallantoic membrane (CAM) angiogenesis assay

This assay is performed essentially as described by Nguyen et al (*Microvascular Res.* 47:31–40 (1994)). A mesh containing either angiogenic factors (bFGF) or tumor cells plus inhibitors is placed onto the CAM of an 8-day old chick embryo and the CAM observed for 3–9 days after implantation of the sample. Angiogenesis is quantitated by determining the percentage of squares in the mesh which contain blood vessels.

D. Xenograft model of subcutaneous (s.c.) tumor growth

Nude mice are inoculated with MDA-MB-231 cells (human breast carcinoma) and Matrigel® (1×10$^6$ cells in 0.2 mL) s.c. in the right flank of the animals. The tumors are staged to 200 mm$^3$ and then treatment with a test composition is initiated (100 $\mu$g/animal/day given q.d. IP). Tumor volumes are obtained every other day and the animals are sacrificed after 2 weeks of treatment. The tumors are excised, weighed and paraffin embedded. Histological sections of the tumors are analyzed by H and E, anti-CD31, Ki-67, TUNEL, and CD68 staining.

E. Xenograft Model of Metastasis

The compounds of this invention are also tested for inhibition of late metastasis using an experimental metastasis model (Crowley, C. W. et al., *Proc. Natl. Acad Sci. USA* 90 5021–5025 (1993)). Late metastasis involves the steps of attachment and extravasation of tumor cells, local invasion, seeding, proliferation and angiogenesis. Human prostatic carcinoma cells (PC-3) transfected with a reporter gene, preferably the green fluorescent protein (GFP) gene, but as an alternative with a gene encoding the enzymes chloramphenicol acetyl-transferase (CAT), luciferase or LacZ, are inoculated into nude mice. This permits utilization of either of these markers (fluorescence detection of GFP or histochemical colorimetric detection of enzymatic activity) to follow the fate of these cells. Cells are injected, preferably iv, and metastases identified after about 14 days, particularly in the lungs but also in regional lymph nodes, femurs and brain. This mimics the organ tropism of naturally occurring metastases in human prostate cancer. For example, GFP-expressing PC-3 cells (1×10$^6$ cells per mouse) are injected iv into the tail veins of nude (nu/nu) mice. Animals are treated with a test composition at 100 $\mu$g/animal/day given q.d. IP. Single metastatic cells and foci are visualized and quantitated by fluorescence microscopy or light microscopic histochemistry or by grinding the tissue and quantitative colorimetric assay of the detectable label.

For a compound to be useful in accordance with this invention, it should demonstrate activity in at least one of the above (in vitro or in vivo) assay systems.

Diagnostic and Prognostic Compositions

The cyclic peptides of the invention have been designed so that they can be detectably labeled and used, for example, to detect a peptide binding site or receptor (such as uPAR) on the surface or in the interior of a cell. The fate of the peptide during and after binding can be followed in vitro or in vivo by using the appropriate method to detect the label. The labeled peptide may be utilized in vivo for diagnosis and prognosis, for example to image occult metastatic foci or for other types of in situ evaluations.

Suitable detectable labels include radioactive, fluorescent, fluorogenic, chromogenic, or other chemical labels. Useful radiolabels, which are detected simply by gamma counter, scintillation counter or autoradiography include $^3$H, $^{125}$I, $^{131}$I, $^{35}$S and $^{14}$C. In addition, $^{131}$I is a useful therapeutic isotope (see below).

Common fluorescent labels include fluorescein, rhodamine, dansyl, phycoerythrin, phycocyanin, allophycocyanin, o-phthaldehyde and fluorescamine. The fluorophore, such as the dansyl group, must be excited by light of a particular wavelength to fluoresce. See, for example, Haugland, *Handbook of Fluorescent Probes and Research Chemicals,* Sixth Ed., Molecular Probes, Eugene, Oreg., 1996). Fluorescein, fluorescein derivatives and fluorescein-like molecules such as Oregon Green™ and its derivatives, Rhodamine Green™ and Rhodol Green™, are coupled to amine groups using the isothiocyanate, succinimidyl ester or dichlorotriazinyl-reactive groups. Similarly, fluorophores may also be coupled to thiols using maleimide, iodoacetamide, and aziridine-reactive groups. The long wavelength rhodamines, which are basically Rhodamine Green™ derivatives with substituents on the nitrogens, are among the most photostable fluorescent labeling reagents known. Their spectra are not affected by changes in pH between 4 and 10, an important advantage over the fluoresceins for many biological applications. This group includes the tetramethylrhodamines, X-rhodamines and Texas Red™ derivatives. Other preferred fluorophores for derivatizing the peptide according to this invention are those which are excited by ultraviolet light. Examples include cascade blue, coumarin derivatives, naphthalenes (of which dansyl chloride is a member), pyrenes and pyridyloxazole derivatives. Also included as labels are two related inorganic materials that have recently been described: semiconductor nanocrystals, comprising, for example, cadmium sulfate (Bruchez, M. et al., *Science* 281:2013–2016 (1998), and quantum dots, e.g.,, zinc-sulfide-capped cadmium selenide (Chan, W. C. W. et al., *Science* 281:2016–2018 (1998)).

In yet another approach, the amino group of a cyclic uPAR-targeting peptide is allowed to react with reagents that yield fluorescent products, for example, fluorescamine, dialdehydes such as o-phthaldialdehyde, naphthalene-2,3-dicarboxylate and anthracene-2,3-dicarboxylate. 7-nitrobenz-2-oxa-1,3-diazole (NBD) derivatives, both chloride and fluoride, are useful to modify amines to yield fluorescent products.

The peptides of the invention can also be labeled for detection using fluorescence-emitting metals such as $^{152}$Eu, or others of the lanthanide series. These metals can be attached to the peptide using such metal chelating groups as diethylenetriaminepentaacetic acid (DTPA, see Example X, infra) or ethylenediaminetetraacetic acid (EDTA). DTPA, for example, is available as the anhydride, which can readily modify the NH$_2$-containing uPAR-targeting peptides of this invention.

For in vivo diagnosis or therapy, radionuclides may be bound to the cyclic peptide either directly or indirectly using a chelating agent such as DTPA and EDTA. Examples of such radionuclides are $^{99}$Tc, $^{123}$I, $^{125}$I, $^{131}$I, $^{111}$In, $^{97}$Ru, $^{67}$Cu, $^{67}$Ga, $^{68}$Ga, $^{72}$As, $^{89}$Zr, $^{90}$Y and $^{201}$Tl. Generally, the amount of labeled peptide needed for detectability in diagnostic use will vary depending on considerations such as age, condition, sex, and extent of disease in the patient, contraindications, if any, and other variables, and is to be adjusted by the individual physician or diagnostician. Dosage can vary from 0.01 mg/kg to 100 mg/kg.

The cyclic peptides can also be made detectable by coupling them to a phosphorescent or a chemiluminescent compound. The presence of the chemiluminescent-tagged peptide is then determined by detecting the presence of luminescence that arises during the course of a chemical reaction. Examples of particularly useful chemiluminescers are luminol, isoluminol, theromatic acridinium ester, imidazole, acridinium salt and oxalate ester. Likewise, a bioluminescent compound may be used to label the peptides. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

In yet another embodiment, colorimetric detection is used, based on chromogenic compounds which have, or result in, chromophores with high extinction coefficients.

In situ detection of the labeled peptide may be accomplished by removing a histological specimen from a subject and examining it by microscopy under appropriate conditions to detect the label. Those of ordinary skill will readily perceive that any of a wide variety of histological methods (such as staining procedures) can be modified in order to achieve such in situ detection.

The term "diagnostically labeled" means that the peptide has attached to it a diagnostically detectable label. There are many different labels and methods of labeling known to those of ordinary skill in the art. Examples of the types of labels which can be used in the present invention include radioactive isotopes, paramagnetic isotopes, and compounds which can be imaged by positron emission tomography (PET). Those of ordinary skill in the art will know of other suitable labels for binding to the peptides used in the invention, or will be able to ascertain such, by routine experimentation.

For diagnostic in vivo radioimaging, the type of detection instrument available is a major factor in selecting a radionuclide. The radionuclide chosen must have a type of decay which is detectable by a particular instrument. In general, any conventional method for visualizing diagnostic imaging can be utilized in accordance with this invention. Another factor in selecting a radionuclide for in vivo diagnosis is that its half-life be long enough so that the label is still detectable at the time of maximum uptake by the target tissue, but short enough so that deleterious irradiation of the host is minimized. In one preferred embodiment, a radionuclide used for in vivo imaging does not emit particles, but produces a large number of photons in a 140–200 keV range, which may be readily detected by conventional gamma cameras.

In vivo imaging may be used to detect occult metastases which are not observable by etaF- other methods. The expression of uPAR correlates with progression of diseases in cancer patients such that patients with late stage cancer have higher levels of uPAR in both their primary tumors and metastases. uPAR-targeted imaging could be used to stage tumors non- invasively or to detect other diseases which are associated with the presence of increased levels of uPAR (for example, restenosis that occurs following angioplasty).

Reagent Compositions

In another embodiment, the peptides or derivatives of the present invention are used as affinity ligands for binding to uPAR in assays, preparative affinity chromatography and solid phase separation of uPAR. Such compositions may also be used to identify, enrich, purify or isolate cells to which the peptide or derivative binds, preferably through a specific receptor-ligand interaction using flow cytometric and/or solid phase methodologies. The peptide or derivative is immobilized using conventional methods, e.g. binding to CNBr- activated Sepharose® or Agarose®, NHS-Agarose® or Sepharose®, epoxy-activated Sepharose® or Agarose®, EAH-Sepharose® or Agarose®, streptavidin-Sepharose® or Agarose® in conjunction with biotinylated peptide or derivatives. In general the peptides or derivatives of the invention may be immobilized by any other method which is capable of immobilizing these compounds to a solid phase for the indicated purposes. See, for example *Affinity Chromatography: Principles and Methods* (*Pharmacia LKB Biotechnology*). Thus, one embodiment is a composition comprising any of the peptides, derivatives or peptidomimetics described herein, bound to a solid support or a resin. The compound may be bound directly or via a spacer, preferably an aliphatic chain having about 2–12 carbon atoms.

By "solid phase" or "solid support" or "carrier" is intended any support or carrier capable of binding the peptide or derivative. Well-known supports, or carriers, in addition to Sepharose® or Agarose® described above are glass, polystyrene, polypropylene, polyethylene, dextran, nylon, amylases, natural and modified celluloses such as nitrocellulose, polyacrylamides, polyvinylidene difluoride, other agaroses, and magnetite, including magnetic beads.. The carrier can be totally insoluble or partially soluble. The support material may have any possible structural configuration so long as the coupled molecule is capable of binding to receptor material. Thus, the support configuration may be spherical, as in a bead, or cylindrical, as in the inside surface of a test tube or microplate well, or the external surface of a rod. Alternatively, the surface may be flat such as a sheet, test strip, bottom surface of a microplate well, etc.

The compositions of the present invention may be used in diagnostic, prognostic or research procedures in conjunction with any appropriate cell, tissue, organ or biological sample of the desired animal species. By the term "biological sample" is intended any fluid or other material derived from the body of a normal or diseased subject, such as blood, serum, plasma, lymph, urine, saliva, tears, cerebrospinal fluid, milk, amniotic fluid, bile, ascites fluid, pus and the like. Also included within the meaning of this term is a organ or tissue extract and a culture fluid in which any cells or tissue preparation from the subject has been incubated.

Pharmaceutical and Therapeutic Compositions and Their Administration

The compounds that may be employed in the pharmaceutical compositions of the invention include all of those compounds described above, as well as the pharmaceutically acceptable salts of these compounds. Pharmaceutically acceptable acid addition salts of the compounds of the invention containing a basic group are formed where appropriate with strong or moderately strong, non-toxic, organic or inorganic acids by methods known to the art. Exemplary of the acid addition salts that are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts.

Pharmaceutically acceptable base addition salts of compounds of the invention containing an acidic group are prepared by known methods from organic and inorganic bases and include, for example, nontoxic alkali met al and alkaline earth bases, such as calcium, sodium, potassium and ammonium hydroxide; and nontoxic organic bases such as triethylamine, butylamine, piperazine, and tri(hydroxymethyl)methylamine.

As stated above, the compounds of the invention possess the ability to inhibit invasiveness or angiogenesis, properties that are exploited in the treatment of cancer, in particular metastatic cancer. A composition of this invention may be active per se, or may act as a "pro-drug" that is converted in vivo to the active form.

The compounds of the invention, as well as the pharmaceutically acceptable salts thereof, may be incorporated into convenient dosage forms, such as capsules, impregnated wafers, tablets or injectable preparations. Solid or liquid pharmaceutically acceptable carriers may be employed.

Preferably, the compounds of the invention are administered systemically, e.g., by injection. When used, injection may be by any known route, preferably intravenous, subcutaneous, intramuscular, intracranial or intraperitoneal. Injectables can be prepared in conventional forms, either as solutions or suspensions, solid forms suitable for solution or suspension in liquid prior to injection, or as emulsions.

Solid carriers include starch, lactose, calcium sulfate dihydrate, terra alba, sucrose, talc, gelatin, agar, pectin, acacia, magnesium stearate and stearic acid. Liquid carriers include syrup, peanut oil, olive oil, saline, water, dextrose, glycerol and the like. Similarly, the carrier or diluent may include any prolonged release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g., a solution), such as an ampoule, or an aqueous or nonaqueous liquid suspension. A summary of such pharmaceutical compositions may be found, for example, in *Remington's Pharmaceutical Sciences,* Mack Publishing Company, Easton Pa.(Gennaro 18th ed. 1990).

The pharmaceutical preparations are made following conventional techniques of pharmaceutical chemistry involving such steps as mixing, granulating and compressing, when necessary for tablet forms, or mixing, filling and dissolving the ingredients, as appropriate, to give the desired products for oral, parenteral, topical, transdermal, intravaginal, intrapenile, intranasal, intrabronchial, intracranial, intraocular, intraaural and rectal administration. The pharmaceutical compositions may also contain minor amounts of nontoxic auxiliary substances such as wetting or emulsifying agents, pH buffering agents and so forth.

The present invention may be used in the diagnosis or treatment of any of a number of animal genera and species, and are equally applicable in the practice of human or veterinary medicine. Thus, the pharmaceutical compositions can be used to treat domestic and commercial animals, including birds and more preferably mammals, as well as humans.

Though the preferred routes of administration are systemic the pharmaceutical composition may be administered topically or transdermally, e.g., as an ointment, cream or gel; orally; rectally; e.g., as a suppository, parenterally, by injection or continuously by infusion; intravaginally; intrapenilely; intranasally; intrabronchially; intracranially, intraaurally; or intraocularly.

For topical application, the compound may be incorporated into topically applied vehicles such as a salve or ointment. The carrier for the active ingredient may be either in sprayable or nonsprayable form. Non-sprayable forms can be semi-solid or solid forms comprising a carrier indigenous to topical application and having a dynamic viscosity preferably greater than that of water. Suitable formulations include, but are not limited to, solution, suspensions, emulsions, creams, ointments, powders, liniments, salves, and the like. If desired, these may be sterilized or mixed with auxiliary agents, e.g., preservatives, stabilizers, wetting agents, buffers, or salts for influencing osmotic pressure and the like. Preferred vehicles for non-sprayable topical preparations include ointment bases, e.g., polyethylene glycol-1000 (PEG-1000); conventional creams such as HEB cream; gels; as well as petroleum jelly and the like.

Also suitable for topic application are sprayable aerosol preparations wherein the compound, preferably in combination with a solid or liquid inert carrier material, is packaged in a squeeze bottle or in admixture with a pressurized volatile, normally gaseous propellant. The aerosol preparations can contain solvents, buffers, surfactants, perfumes, and/or antioxidants in addition to the compounds of the invention.

For the preferred topical applications, especially for humans, it is preferred to administer an effective amount of the compound to an infected area, e.g., skin surface, mucous membrane, eyes, etc. This amount will generally range from about 0.001 mg to about 1 g per application, depending upon the area to be treated, the severity of the symptoms, and the nature of the topical vehicle employed.

Therapeutic compositions of the invention may comprise, in addition to the modified cyclic peptide, one or more additional anti-tumor agents, such as mitotic inhibitors, e.g., vinblastine; alkylating agents, e.g., cyclophosphamide; folate inhibitors, e.g., methotrexate, piritrexim or trimetrexate; antimetabolites, e.g., 5-fluorouracil and cytosine arabinoside; intercalating antibiotics, e.g., adriamycin and bleomycin; enzymes or enzyme inhibitors, e.g., asparaginase, topoisomerase inhibitors such as etoposide; or biological response modifiers, e.g., interferons or interleukins. In fact, pharmaceutical compositions comprising any known cancer therapeutic in combination with the cyclic peptides disclosed herein are within the scope of this invention. The pharmaceutical composition may also comprise one or more other medicaments to treat additional symptoms for which the target patients are at risk, for example, anti-infectives including antibacterial, anti-fungal, anti-parasitic, anti-viral, and anti-coccidial agents.

Other Therapeutic Compositions

In another embodiment, the compounds of this invention are "therapeutically conjugated" and used to deliver a therapeutic agent to the site to which the compounds home and bind, such as sites of tumor metastasis or foci of infection/inflammation. The term "therapeutically conjugated" means that the modified cyclic peptide or peptidomimetic is conjugated to another therapeutic agent that is directed either to the underlying cause or to a "component" of tumor invasion, angiogenesis or inflammation.

Examples of therapeutic radioisotopes useful herein include $^{125}I$, $^{131}I$, $^{90}Y$, $^{67}Cu$, $^{217}Bi$, $^{211}At$, $^{212}Pb$, $^{47}Sc$, and $^{109}Pd$. These atoms can be conjugated to the peptide compounds directly, indirectly as part of a chelate (see Example X), or, in the case of iodine, indirectly as part of an iodinated Bolton-Hunter group. The radioiodine can be introduced either before or after this group is coupled to the peptide compound (see Example IX, below).

Preferred doses of the radionuclide conjugates are a function of the specific radioactivity to be delivered to the target site which varies with tumor type, tumor location and vascularization, kinetics and biodistribution of the cyclic peptide carrier, energy of radioactive emission by the nuclide, etc. Those skilled in the art of radiotherapy can readily adjust the dose of the cyclic peptide in conjunction with the dose of the particular nuclide to effect the desired therapeutic benefit without undue experimentation. For example, an effective dose of $^{131}I$-RTLPPD is between about 1 and 1000 μCi per gram of tumor for an extracranial tumor.

Another therapeutic approach included here is the use of boron neutron capture therapy, where a boronated cyclic peptide is delivered to a desired target site, such as a tumor, most preferably an intracranial tumor (Barth, R. F., *Cancer Invest.* 14:534–550 (1996); Mishima, Y. (ed.), *Cancer Neutron Capture Therapy,* New York: Plenum Publishing Corp., 1996; Soloway, A. H., et al., (eds), *J. Neuro-Oncol.* 33:1–188 (1997). The stable isotope $^{10}B$ is irradiated with low energy (<0.025 eV) thermal neutrons, and the resulting nuclear capture yields α particles and $^{7}Li$ nuclei which have high linear energy transfer and respective path lengths of about 9 and 5 μm. This method is predicated on $^{10}B$ accumulation in the tumor with lower levels in blood, endothelial cells and normal tissue (e.g., brain). Such delivery has been accomplished using epidermal growth factor (Yang. W. et al., *Cancer Res* 57:4333–4339 (1997). Because of the selective expression of uPAR in tumors, the cyclic peptides of the present invention are excellent delivery vehicles for this therapeutic moiety.

Other therapeutic agents which can be coupled to the peptide compounds according to the method of the invention are drugs, prodrugs, enzymes for activating pro-drugs, photo-sensitizing agents, gene therapeutics, antisense vectors, viral vectors, lectins and other toxins.

The therapeutic dosage administered is an amount which is therapeutically effective, as is known to or readily ascertainable by those skilled in the art. The dose is also dependent upon the age, health, and weight of the recipient, kind of concurrent treatment(s), if any, the frequency of treatment, and the nature of the effect desired, such as, for example, anti-inflammatory effects or anti-bacterial effect.

Lectins are proteins, commonly derived from plants, that bind to carbohydrates. Among other activities, some lectins are toxic. Some of the most cytotoxic substances known are protein toxins of bacterial and plant origin (Frankel, A. E. et al., *Ann. Rev. Med* 37:125–142 (1986)). These molecules binding the cell surface and inhibit cellular protein synthesis. The most commonly used plant toxins are ricin and abrin; the most commonly used bacterial toxins are diphtheria toxin and Pseudomonas exotoxin A. In ricin and abrin, the binding and toxic functions are contained in two separate protein subunits, the A and B chains. The ricin B chain binds to the cell surface carbohydrates and promotes the uptake of the A chain into the cell. Once inside the cell, the ricin A chain inhibits protein synthesis by inactivating the 60S subunit of the eukaryotic ribosome Endo, Y. et al., *J. Biol. Chem.* 262: 5908–5912 (1987)). Other plant derived toxins, which are single chain ribosomal inhibitory proteins, include pokeweed antiviral protein, wheat germ protein, gelonin, dianthins, momorcharins, trichosanthin, and many others (Strip, F. et al., *FEBS Lett.* 195:1–8 (1986)). Diphtheria toxin and Pseudomonas exotoxin A are also single chain proteins, and their binding and toxicity functions reside in separate domains of the same protein chain with full toxin activity requiring proteolytic cleavage between the two domains. Pseudomonas exotoxin A has the same catalytic activity as diphtheria toxin. Ricin has been used therapeutically by binding its toxic α-chain, to targeting molecules such as antibodies to enable site-specific delivery of the toxic effect. Bacterial toxins have also been used as anti-tumor conjugates. As intended herein, a toxic peptide chain or domain is conjugated to a compound of this invention and delivered in a site-specific manner to a target site where the toxic activity is desired, such as a metastatic focus. Conjugation of toxins to protein such as antibodies or other ligands are known in the art (Olsnes, S. et al., *Immunol. Today* 10:291–295 (1989); Vitetta, E. S. et al., *Ann. Rev. Immunol.* 3:197–212 (1985)).

Cytotoxic drugs that interfere with critical cellular processes including DNA, RNA, and protein synthesis, have been conjugated to antibodies and subsequently used for in vivo therapy. Such drugs, including, but not limited to, daunorubicin, doxorubicin, methotrexate, and Mitomycin C are also coupled to the compounds of this invention and used therapeutically in this form.

In another embodiment of the invention, photosensitizers may be coupled to the compounds of the invention for delivery directly to a tumor.

Therapeutic Methods

The methods of this invention may be used to inhibit tumor growth and invasion in a subject or to suppress angiogenesis induced by tumors by inhibiting endothelial cell growth and migration. By inhibiting the growth or invasion of a tumor or angiogenesis, the methods result in inhibition of tumor metastasis. A vertebrate subject, preferably a mammal, more preferably a human, is administered an amount of the compound effective to inhibit tumor growth, invasion or angiogenesis. The compound or pharmaceutically acceptable salt thereof is preferably administered in the form of a pharmaceutical composition as described above.

Doses of the compounds preferably include pharmaceutical dosage units comprising an effective amount of the peptide. By an effective amount is meant an amount sufficient to achieve a steady state concentration in vivo which results in a measurable reduction in any relevant parameter of disease and may include growth of primary or metastatic tumor, any accepted index of inflammatory reactivity, or a measurable prolongation of disease-free interval or of survival. For example, a reduction in tumor growth in 20% of patients is considered efficacious (Frei III, E., *The Cancer Journal* 3:127–136 (1997)). However, an effect of this magnitude is not considered to be a minimal requirement for the dose to be effective in accordance with this invention.

In one embodiment, an effective dose is preferably 10-fold and more preferably 100-fold higher than the 50% effective dose ($ED_{50}$) of the compound in an in vivo assay as described herein.

The amount of active compound to be administered depends on the precise peptide or derivative selected, the disease or condition, the route of administration, the health and weight of the recipient, the existence of other concurrent treatment, if any, the frequency of treatment, the nature of the effect desired, for example, inhibition of tumor metastasis, and the judgment of the skilled practitioner.

A preferred dose for treating a subject, preferably mammalian, more preferably human, with a tumor is an amount of up to about 100 milligrams of active compound per kilogram of body weight. A typical single dosage of the peptide or peptidomimetic is between about 1 ng and about 100 mg/kg body weight. For topical administration, dosages in the range of about 0.01–20% concentration (by weight) of the compound, preferably 1–5%, are suggested. A total daily dosage in the range of about 0.1 milligrams to about 7 grams is preferred for intravenous administration. The foregoing ranges are, however, suggestive, as the number of variables in an individual treatment regime is large, and considerable excursions from these preferred values are expected.

An effective amount or dose of the peptide for inhibiting invasion in vitro is in the range of about 1 picogram to about 0.5 nanograms per cell. Effective doses and optimal dose ranges may be determined in vitro using the methods described herein.

The compounds of the invention may be characterized as producing an inhibitory effect on cell migration and invasion, tumor cell and endothelial cell proliferation, on angiogenesis, on tumor metastasis or on inflammatory reactions. The compounds are especially useful in producing an anti-tumor effect in a mammalian host, preferably human, harboring a tumor.

The foregoing compositions and treatment methods are useful for inhibiting cell migration and invasion or cell proliferation in a subject having any disease or condition associated with undesired cell invasion, proliferation, angiogenesis or metastasis. Such diseases or conditions may include primary growth of solid tumors or leukemias and lymphomas, metastasis, invasion and/or growth of tumor metastases, benign hyperplasias, atherosclerosis, myocardial angiogenesis, post-balloon angioplasty vascular restenosis, neointima formation following vascular trauma, vascular graft restenosis, deep venous thrombosis, ischemic limb angiogenesis, telangiectasia, pyogenic granuloma, corneal diseases, rubeosis, neovascular glaucoma, diabetic and other retinopathy, retrolental fibroplasia, diabetic neovascularization, macular degeneration, endometriosis, arthritis, fibrosis associated with chronic inflammatory conditions including psoriasis scleroderma, lung fibrosis, chemotherapy-induced fibrosis, wound healing with scarring and fibrosis, peptic ulcers, fractures, keloids, and disorders of vasculogenesis, hematopoiesis, ovulation, menstruation, pregnancy and placentation, or any other disease or condition in which invasion or angiogenesis is pathogenic or undesired.

More recently, it has become apparent that angiogenesis inhibitors may play a role in preventing inflammatory angiogenesis and gliosis following traumatic spinal cord injury, thereby promoting the reestablishment of neuronal connectivity (Wamil, A. W. et al., *Proc. Nat'l. Acad Sci. USA* 95:13188–13193 (1998)). Therefore, the compositions of the present invention are administered as soon as possible after traumatic spinal cord injury and for several days up to about two weeks thereafter to inhibit the angiogenesis and gliosis that would sterically prevent reestablishment of neuronal connectivity. The treatment reduces the area of damage at the site of spinal cord injury and facilitates regeneration of neuronal function and thereby prevents paralysis. The compounds of the invention are expected also to protect axons from Wallerian degeneration, reverse aminobutyrate-mediated depolarization (occurring in traumatized neurons), and improve recovery of neuronal conductivity of isolated central nervous system cells and tissue in culture.

Having now generally described the invention, the same will be more readily understood through reference to the following examples which are provided by way of illustration, and are not intended to be limiting of the present invention, unless specified.

EXAMPLE I

Synthesis of

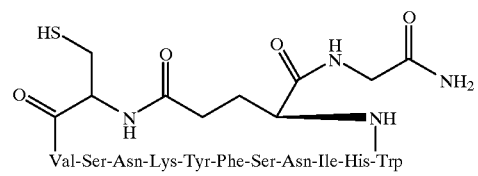

Val-Ser-Asn-Lys-Tyr-Phe-Ser-Asn-Ile-His-Trp

The starting material is MBHA resin substituted at a level of 0.45 mEq/gm resin. Each of the remaining L-amino acids is added in sequence in a synthesis cycle consisting of:

(1) TFA De-protection

The BOC protecting group is removed from the α-amino nitrogen of the starting material by treating the resin with 50% trifluoroacetic acid (TFA) in dichloromethane (DCM) (two to three volumes per resin volume). The mixture is stirred at room temperature for 30 minutes and then drained. The resin is then washed once with an equal volume of isopropanol for one minute and then washed twice with an equal volume of methanol, each wash taking one minute.

(2) Coupling

The deprotected resin is washed twice with an equal volume of 10% triethylamine in DCM, each wash taking one minute, and washed twice with an equal volume of methanol, each wash taking one minute, and washed twice with an equal volume of DCM, each wash taking one minute. A BOC-protected amino acid (three equivalents, dissolved in DCM or in a mixture of DCM and N,N-dimethylformamide (DMF)) and 1-hydroxybenzotriazole (HOBT) (1M solution in DMF, three equivalents) is added to the resin and the mixture is stirred for a few seconds.

Dicyclohexylcarbodiimide (DCC) (1M solution in DCM, three equivalents) is then added and the whole mixture is stirred for 60–120 minutes. The resin is washed twice with an equal volume of methanol and then washed twice with an equal volume of DCM. A small sample is taken for a ninhydrin test to assess the completeness of coupling. Generally, if incomplete, the coupling step 2 is repeated. If complete, the synthesis is continued with the capping step 3. All amino acids are used as α-BOC derivatives. Side chain protecting groups are as follows:

| | |
|---|---|
| Glutamic acid | Cyclohexyl ester |
| Tryptophan | N-Formyl |
| Histidine | Benzyloxymethyl |
| Asparagine | Xanthyl |
| Serine | O-Benzyl |
| Tyrosine | 2-Bromo-Z |
| Lysine | Trifluoroacetyl |
| Cysteine | Acetamidomethyl |

(3) Capping

The resin is stirred with an equal volume of acetic anhydride (20% solution in DCM) for 5 minutes at room temperature. The resin is washed twice with an equal volume of methanol and twice with an equal volume of DCM.

(4) HF Cleavage

The resin bearing the desired amino acid sequence (1.0 gram) is placed in a Teflon reaction vessel, and anhydrous anisole (1 mL) is added. The vessel is cooled with liquid $N_2$, and anhydrous HF (10 mL) is distilled into it. The temperature is raised with iced water to 0° C. The mixture is stirred at this temperature for 1 hour, and then the HF is distilled off at 0° C. The residue is washed with anhydrous ether, and the peptide is extracted with a 1:1 mixture of $CH_3CN:H_2O$.

(5) Cyclization

The linear peptide (0.1 mmole) is dissolved in DMSO (50 mL), and the resulting solution is diluted with DMF (100 mL). TBTU (5 equivalents) and HOBT (5 equivalents) are added to the solution; these reagents dissolve. The pH is adjusted to 7.5–8.0 with N,N-diisopropylethylamine. Cyclization is monitored by analytical HPLC and is found to be complete after 120 minutes.

(6) Purification

The above cyclic peptide solution is acidified to pH 4.0, diluted 5-fold with water, and directly loaded onto a Waters C18 preparative column (2 inches diameter, 15–20 μm particle size, 300 Å pore size). The loaded column is eluted with a two-component eluent applied as a linear gradient, starting with 15% of solution A in solution B and finishing with 40% of solution A in solution B. Solution A is 0.1% TFA in $H_2O$ and solution B is 0.1% TFA in $CH_3CN$. Fractions exhibiting purity equal to or better than that desired are pooled and lyophilized to render the purified, trifluoroacetyl-protected product as the trifluoroacetate salt.

(7) Removal of the Trifluoroacetyl Protecting Group

The pure, (ε-TFA)-Lys-protected peptide is dissolved in a mixture of dioxane-water (1: 1) and the resulting solution is diluted 2-fold with 0.2N $NaOH_{aq}$. After 15 minutes the mixture is acidified to pH 4.0, diluted 3-fold with water, and directly loaded onto a Waters C18 preparative column (2 inches diameter, 15–20 μm particle size, 300 Å pore size). The loaded column is eluted with a two-component eluent applied as a linear gradient, starting with 15% of solution A in solution B and finishing with 40% of solution A in solution B. Solution A is 0.1% TFA in $H_2O$ and solution B is 0.1% TFA in $CH_3CN$. Fractions exhibiting purity equal to or better than that desired are pooled and lyophilized to render the purified, final product as the trifluoroacetate salt.

(8) Removal of the Acetamidomethyl Protecting Group

The pure, acetamidomethyl-protected peptide is dissolved in 1M acetic acid (approximately 10 mL of acetic acid per millimole of peptide). Mercuric chloride (1.1) equivalents dissolved in 1M aqueous acetic acid (5 mL per millimole of peptide) is added to the peptide solution. The mixture is stirred at room temperature for 2 hours. The resulting mercury complex is decomposed by the addition of a large excess (10 equivalents) of 2-mercapto-ethanol. The precipitate is filtered off and is washed with 1M aqueous acetic acid (2 mL). The filtrate is directly loaded onto a Waters C18 preparative column (2 inches diameter, 15–20 μm particle size, 300 Å pore size). The loaded column is eluted with a two-component eluent applied as a linear gradient, starting with 15% of solution A in solution B and finishing with 40% of solution A in solution B. Solution A is 0.1% TFA in $H_2O$ and solution B is 0.1% TFA in $CH_3CN$. Fractions exhibiting purity equal to or better than that desired are pooled and lyophilized to render the purified, final product as the trifluoroacetate salt.

EXAMPLE II

Synthesis of:

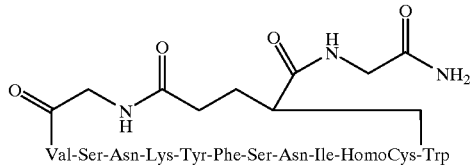

Val-Ser-Asn-Lys-Tyr-Phe-Ser-Asn-Ile-HomoCys-Trp

The starting material is MBHA resin substituted at a level of 0.45 mEq/gm resin. Each of the remaining L-amino acids is added in sequence in a synthesis cycle consisting of:

(1) TFA De-protection

The BOC protecting group is removed from the α-amino nitrogen of the starting material by treating the resin with 50% trifluoroacetic acid (TFA) in dichloromethane (DCM) (two to three volumes per resin volume). The mixture is stirred at room temperature for 30 minutes and then drained. The resin is then washed once with an equal volume of isopropanol for one minute and then washed twice with an equal volume of methanol, each wash taking one minute.

(2) Coupling

The deprotected resin is washed twice with an equal volume of 10% triethylamine in DCM, each wash taking one minute, and washed twice with an equal volume of methanol, each wash taking one minute, and washed twice with an equal volume of DCM, each wash taking one minute. A BOC-protected amino acid (three equivalents, dissolved in DCM or in a mixture of DCM and N,N-dimethylformamide (DMF)) and 1-hydroxybenzotriazole (HOBT) (1M solution in DMF, three equivalents) is added to the resin and the mixture is stirred for a few seconds. Dicyclohexylcarbodiimide (DCC) (1M solution in DCM, three equivalents) is then added and the whole mixture is stirred for 60–120 minutes. The resin is washed twice with an equal volume of methanol and then washed twice with an equal volume of DCM. A small sample is taken for a ninhydrin test to assess the completeness of coupling. Generally, if incomplete, the coupling step 2 is repeated. If complete, the synthesis is continued with the capping step 3. All amino acids are used as α-BOC derivatives. Side chain protecting groups are as follows:

| | |
|---|---|
| Glutamic acid | Cyclohexyl ester |
| Tryptophan | N-Formyl |
| Histidine | Benzyloxymethyl |
| Asparagine | Xanthyl |
| Serine | O-Benzyl |
| Tyrosine | 2-Bromo-Z |
| Lysine | Trifluoroacetyl |
| Homocysteine | Acetamidomethyl |

(3) Capping

The resin is stirred with an equal volume of acetic anhydride (20% solution in DCM) for 5 minutes at room temperature. The resin is washed twice with an equal volume of methanol and twice with an equal volume of DCM.

(4) HF Cleavage

The resin bearing the desired amino acid sequence (1.0 gram) is placed in a Teflon reaction vessel, and anhydrous anisole (1 mL) is added. The vessel is cooled with liquid $N_2$, and anhydrous HF (10 mL) is distilled into it. The temperature is raised with iced water to 0° C. The mixture is stirred at this temperature for 1 hour, and then the HF is distilled off at 0° C. The residue is washed with anhydrous ether, and the peptide is extracted with a 1:1 mixture of $CH_3CN:H_2O$.

(5) Cyclization

The linear peptide (0.1 mmole) is dissolved in DMSO (50 mL), and the resulting solution is diluted with DMF (100 mL). TBTU (5 equivalents) and HOBT (5 equivalents) are added to the solution; these reagents dissolve. The pH is adjusted to 7.5–8.0 with N,N-diisopropylethylamine. Cyclization is monitored by analytical HPLC and is found to be complete after 120 minutes.

(6) Purification

The above cyclic peptide solution is acidified to pH 4.0, diluted 5-fold with water, and directly loaded onto a Waters C18 preparative column (2 inches diameter, 15–20 μm particle size, 300 Å pore size). The loaded column is eluted with a two-component eluent applied as a linear gradient, starting with 15% of solution A in solution B and finishing with 40% of solution A in solution B. Solution A is 0.1% TFA in $H_2O$ and solution B is 0.1% TFA in $CH_3CN$. Fractions exhibiting purity equal to or better than that desired are pooled and lyophilized to render the purified, trifluoroacetyl-protected product as the trifluoroacetate salt.

(7) Removal of the Trifluoroacetyl Protecting Group

The pure, (ε-TFA)-Lys-protected peptide is dissolved in a mixture of dioxane-water (1:1) and the resulting solution is diluted 2-fold with 0.2N $NaOH_{aq}$. After 15 minutes the mixture is acidified to pH 4.0, diluted 3-fold with water, and directly loaded onto a Waters C18 preparative column (2 inches diameter, 15–20 μm particle size, 300A pore size). The loaded column is eluted with a two-component eluent applied as a linear gradient, starting with 15% of solution A in solution B and finishing with 40% of solution A in solution B. Solution A is 0.1% TFA in $H_2O$ and solution B is 0.1% TFA in $CH_3CN$. Fractions exhibiting purity equal to or better than that desired are pooled and lyophilized to render the purified, final product as the trifluoroacetate salt.

(8) Removal of the Acetamidomethyl Protecting Group

The pure, acetamidomethyl-protected peptide is dissolved in 1M acetic acid (approximately 10 mL of acetic acid per millimole of peptide). Mercuric chloride (1.1) equivalents dissolved in 1M aqueous acetic acid (5 mL per millimole of peptide) is added to the peptide solution. The mixture is stirred at room temperature for 2 hours. The resulting mercury complex is decomposed by the addition of a large excess (10 equivalents) of 2-mercapto-ethanol. The precipitate is filtered off and is washed with 1M aqueous acetic acid (2 mL). The filtrate is directly loaded onto a Waters C 18 preparative column (2 inches diameter, 15–20 μm particle size, 300 Å pore size). The loaded column is eluted with a two-component eluent applied as a linear gradient, starting with 15% of solution A in solution B and finishing with 40% of solution A in solution B. Solution A is 0.1% TFA in $H_2O$ and solution B is 0.1% TFA in $CH_3CN$. Fractions exhibiting purity equal to or better than that desired are pooled and lyophilized to render the purified, final product as the trifluoroacetate salt.

EXAMPLE III

Synthesis of:

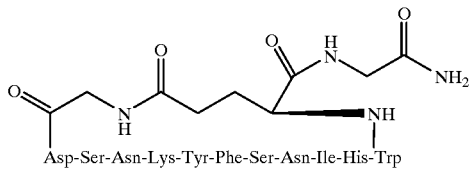

Asp-Ser-Asn-Lys-Tyr-Phe-Ser-Asn-Ile-His-Trp

The starting material is MBHA resin substituted at a level of 0.45 mEq/gm resin. Each of the remaining L-amino acids is added in sequence in a synthesis cycle consisting of:

(1) TFA De-protection

The BOC protecting group is removed from the α-amino nitrogen of the starting material by treating the resin with 50% trifluoroacetic acid (TFA) in dichloromethane (DCM) (two to three volumes per resin volume). The mixture is stirred at room temperature for 30 minutes and then drained. The resin is then washed once with an equal volume of isopropanol for one minute and then washed twice with an equal volume of methanol, each wash taking one minute.

(2) Coupling

The deprotected resin is washed twice with an equal volume of 10% triethylamine in DCM, each wash taking one minute, and washed twice with an equal volume of methanol, each wash taking one minute, and washed twice with an equal volume of DCM, each wash taking one minute. A BOC-protected amino acid (three equivalents, dissolved in DCM or in a mixture of DCM and N,N-dimethylformamide (DMF)) and 1-hydroxybenzotriazole (HOBT) (1M solution in DMF, three equivalents) is added to the resin and the mixture is stirred for a few seconds. Dicyclohexylcarbodiimide (DCC) (1M solution in DCM, three equivalents) is then added and the whole mixture is stirred for 60–120 minutes. The resin is washed twice with an equal volume of methanol and then washed twice with an equal volume of DCM. A small sample is taken for a ninhydrin test to assess the completeness of coupling. Generally, if incomplete, the coupling step 2 is repeated. If complete, the synthesis is continued with the capping step 3. All amino acids are used as α-BOC derivatives. Side chain protecting groups are as follows:

| | |
|---|---|
| Glutamic acid | Cyclohexyl ester |
| Tryptophan | N-Formyl |
| Histidine | Benzyloxymethyl |
| Asparagine | Xanthyl |
| Serine | O-Benzyl |

| | |
|---|---|
| Tyrosine | 2-Bromo-Z |
| Lysine | Fluorenylmethyloxycarbonyl |
| Aspartic Acid | Fluorenylmethyl |

(3) Capping

The resin is stirred with an equal volume of acetic anhydride (20% solution in DCM) for 5 minutes at room temperature. The resin is washed twice with an equal volume of methanol and twice with an equal volume of DCM.

(4) HF Cleavage

The resin bearing the desired amino acid sequence (1.0 gram) is placed in a Teflon reaction vessel, and anhydrous anisole (1 mL) is added. The vessel is cooled with liquid $N_2$, and anhydrous HF (10 mL) is distilled into it. The temperature is raised with iced water to 0° C. The mixture is stirred at this temperature for 1 hour, and then the HF is distilled off at 0° C. The residue is washed with anhydrous ether, and the peptide is extracted with a 1:1 mixture of $CH_3CN:H_2O$.

(5) Cyclization

The linear peptide (0.1 mmole) is dissolved in DMSO (50 mL), and the resulting solution is diluted with DMF (100 mL). TBTU (5 equivalents) and HOBT (5 equivalents) are added to the solution; these reagents dissolve. The pH is adjusted to 7.5–8.0 with N,N-diisopropylethylamine. Cyclization is monitored by analytical HPLC and is found to be complete after 120 minutes.

(6) Purification

The above cyclic peptide solution is acidified to pH 4.0, diluted 5-fold with water, and directly loaded onto a Waters C18 preparative column (2 inches diameter, 15–20 μm particle size, 300 Å pore size). The loaded column is eluted with a two-component eluent applied as a linear gradient, starting with 15% of solution A in solution B and finishing with 40% of solution A in solution B. Solution A is 0.1% TFA in $H_2O$ and solution B is 0.1% TFA in $CH_3CN$. Fractions exhibiting purity equal to or better than that desired are pooled and lyophilized to render the purified, trifluoroacetyl-protected product as the trifluoroacetate salt.

(7) Removal of the Fluorenylmethyl-containing Protecting Groups

The pure, (ε-Fluorenylmethyloxycarbonyl)-Lys-(β-Fluorenylmethyl)-Asp-protected peptide is dissolved in a mixture of dioxane-water (1:1) and the resulting solution is diluted 2-fold with 0.2N $NaOH_{aq}$. After 15 minutes the mixture is acidified to pH 4.0, diluted 3-fold with water, and directly loaded onto a Waters C18 preparative column (2 inches diameter, 15–20 μm particle size, 300 Å pore size). The loaded column is eluted with a two-component eluent applied as a linear gradient, starting with 15% of solution A in solution B and finishing with 40% of solution A in solution B. Solution A is 0.1% TFA in $H_2O$ and solution B is 0.1% TFA in $CH_3CN$. Fractions exhibiting purity equal to or better than that desired are pooled and lyophilized to render the purified, final product as the trifluoroacetate salt.

EXAMPLE IV

Synthesis of:

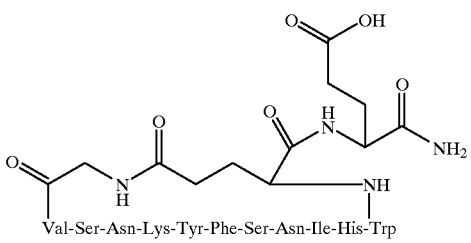

Val-Ser-Asn-Lys-Tyr-Phe-Ser-Asn-Ile-His-Trp

The starting material is MBHA resin substituted at a level of 0.45 mEq/gm resin. Each of the remaining L-amino acids is added in sequence in a synthesis cycle consisting of:

(1) TFA De-protection

The BOC protecting group is removed from the α-amino nitrogen of the starting material by treating the resin with 50% trifluoroacetic acid (TFA) in dichloromethane (DCM) (two to three volumes per resin volume). The mixture is stirred at room temperature for 30 minutes and then drained. The resin is then washed once with an equal volume of isopropanol for one minute and then washed twice with an equal volume of methanol, each wash taking one minute.

(2) Coupling

The deprotected resin is washed twice with an equal volume of 10% triethylamine in DCM, each wash taking one minute, and washed twice with an equal volume of methanol, each wash taking one minute, and washed twice with an equal volume of DCM, each wash taking one minute. A BOC-protected amino acid (three equivalents, dissolved in DCM or in a mixture of DCM and N,N-dimethylformamide (DMF)) and 1-hydroxybenzotriazole (HOBT) (1M solution in DMF, three equivalents) is added to the resin and the mixture is stirred for a few seconds. Dicyclohexylcarbodiimide (DCC) (1M solution in DCM, three equivalents) is then added and the whole mixture is stirred for 60–120 minutes. The resin is washed twice with an equal volume of methanol and then washed twice with an equal volume of DCM. A small sample is taken for a ninhydrin test to assess the completeness of coupling. Generally, if incomplete, the coupling step 2 is repeated. If complete, the synthesis is continued with the capping step 3. All amino acids are used as a-BOC derivatives. Side chain protecting groups are as follows:

| | |
|---|---|
| Glutamic acid exocyclic | Fluorenylmethyl |
| Glutamic acid endocyclic | Cyclohexyl ester |
| Tryptophan | N-Formyl |
| Histidine | Benzyloxymethyl |
| Asparagine | Xanthyl |
| Serine | O-Benzyl |
| Tyrosine | 2-Bromo-Z |
| Lysine | Fluroenylmethyloxycarbonyl |

(3) Capping

The resin is stirred with an equal volume of acetic anhydride (20% solution in DCM) for 5 minutes at room temperature. The resin is washed twice with an equal volume of methanol and twice with an equal volume of DCM.

(4) HF Cleavage

The resin bearing the desired amino acid sequence (1.0 gram) is placed in a Teflon reaction vessel, and anhydrous anisole (1 mL) is added. The vessel is cooled with liquid N₂, and anhydrous HF (10 mL) is distilled into it. The temperature is raised with iced water to 0° C. The mixture is stirred at this temperature for 1 hour, and then the HF is distilled off at 0° C. The residue is washed with anhydrous ether, and the peptide is extracted with a 1:1 mixture of CH₃CN:H₂O.

(5) Cyclization

The linear peptide (0.1 mmole) is dissolved in DMSO (50 mL), and the resulting solution is diluted with DMF (100 mL). TBTU (5 equivalents) and HOBT (5 equivalents) are added to the solution; these reagents dissolve. The pH is adjusted to 7.5–8.0 with N,N-diisopropylethylamine. Cyclization is monitored by analytical HPLC and is found to be complete after 120 minutes.

(6) Purification

The above cyclic peptide solution is acidified to pH 4.0, diluted 5-fold with water, and directly loaded onto a Waters C18 preparative column (2 inches diameter, 15–20 μm particle size, 300 Å pore size). The loaded column is eluted with a two-component eluent applied as a linear gradient, starting with 15% of solution A in solution B and finishing with 40% of solution A in solution B. Solution A is 0.1% TFA in H₂O and solution B is 0.1% TFA in CH₃CN. Fractions exhibiting purity equal to or better than that desired are pooled and lyophilized to render the purified, trifluoroacetyl-protected product as the trifluoroacetate salt.

(7) Removal of the Fluorenylmethyl-containing Protecting Groups

The pure, (ε-Fluorenylmethyloxycarbonyl)-Lys-(γ-Fluorenylmethyl)-Glu-protected peptide is dissolved in a mixture of dioxane-water (1:1) and the resulting solution is diluted 2-fold with 0.2N NaOH$_{aq}$. After 15 minutes the mixture is acidified to pH 4.0, diluted 3-fold with water, and directly loaded onto a Waters C18 preparative column (2 inches diameter, 15–20 μm particle size, 300 Å pore size). The loaded column is eluted with a two-component eluent applied as a linear gradient, starting with 15% of solution A in solution B and finishing with 40% of solution A in solution B. Solution A is 0.1% TFA in H₂0 and solution B is 0.1% TFA in CH₃CN. Fractions exhibiting purity equal to or better than that desired are pooled and lyophilized to render the purified, final product as the trifluoroacetate salt.

EXAMPLE V

Synthesis of:

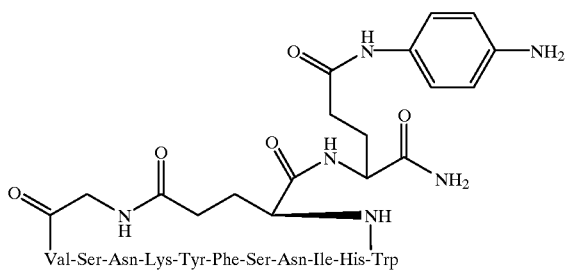

Val-Ser-Asn-Lys-Tyr-Phe-Ser-Asn-Ile-His-Trp 4-((9-Fluorenylmethyloxycarbonyl)amino)aniline is prepared from p-phenylenediamine (2.16 g, 0.02 mole) and N-(9-fluorenylmethoxycarbonyloxy)succinimide (6.75 g, 0.02 mole) in dioxane-water (1:1). Purification is achieved by crystallization. This product is coupled to BOC-L-Glu-α-O-Benzyl using HOBT/DCC. After the usual work-up, the fully-protected amino acid derivative is dissolved in MeOH and treated with hydrogen gas at 1 atmosphere pressure in the presence of palladium-on-carbon catalyst until hydrogen consumption is complete (about 2 hours). Following the usual workup, the starting material:

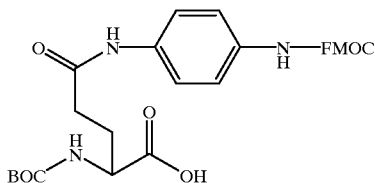

is obtained. It is coupled to the MBHA resin at a level of 0.45 mEq/gm resin. Each of the remaining L-amino acids is added in sequence in a synthesis cycle consisting of:

(1) TFA Deprotection

The BOC protecting group is removed from the α-amino nitrogen of the starting material by treating the resin with 50% trifluoroacetic acid (TFA) in dichloromethane (DCM) (two to three volumes per resin volume). The mixture is stirred at room temperature for 30 minutes and then drained. The resin is then washed once with an equal volume of isopropanol for one minute and then washed twice with an equal volume of methanol, each wash taking one minute.

(2) Coupling

The deprotected resin is washed twice with an equal volume of 10% triethylamine in DCM, each wash taking one minute, and washed twice with an equal volume of methanol, each wash taking one minute, and washed twice with an equal volume of DCM, each wash taking one minute. A BOC-protected amino acid (three equivalents, dissolved in DCM or in a mixture of DCM and N,N-dimethylformamide (DMF)) and 1-hydroxybenzotriazole (HOBT) (1M solution in DMF, three equivalents) is added to the resin and the mixture is stirred for a few seconds. Dicyclohexylcarbodiimide (DCC) (1M solution in DCM, three equivalents) is then added and the whole mixture is stirred for 60–120 minutes. The resin is washed twice with an equal volume of methanol and then washed twice with an equal volume of DCM. A small sample is taken for a ninhydrin test to assess the completeness of coupling. Generally, if incomplete, the coupling step 2 is repeated. If complete, the synthesis is continued with the capping step 3. All amino acids are used as a-BOC derivatives. Side chain protecting groups are as follows:

| | |
|---|---|
| Glutamic acid | Cyclohexyl ester |
| Tryptophan | N-Formyl |
| Histidine | Benzyloxymethyl |
| Asparagine | Xanthyl |
| Serine | O-Benzyl |
| Tyrosine | 2-Bromo-Z |
| Lysine | Trifluoroacetyl |

(3) Capping

The resin is stirred with an equal volume of acetic anhydride (20% solution in DCM) for 5 minutes at room temperature. The resin is washed twice with an equal volume of methanol and twice with an equal volume of DCM.

(4) HF Cleavage

The resin bearing the desired amino acid sequence (1.0 gram) is placed in a Teflon reaction vessel, and anhydrous anisole (1 mL) is added. The vessel is cooled with liquid N₂, and anhydrous HF (10 mL) is distilled into it. The temperature is raised with iced water to 0° C. The mixture is stirred at this temperature for 1 hour, and then the HF is distilled off at 0° C. The residue is washed with anhydrous ether, and the peptide is extracted with a 1:1 mixture of $CH_3CN:H_2O$.

(5) Cyclization

The linear peptide (0.1 mmole) is dissolved in DMSO (50 mL), and the resulting solution is diluted with DMF (100 mL). TBTU (5 equivalents) and HOBT (5 equivalents) are added to the solution; these reagents dissolve. The pH is adjusted to 7.5–8.0 with N,N-diisopropylethylamine. Cyclization is monitored by analytical HPLC and is found to be complete after 120 minutes.

(6) Purification

The above cyclic peptide solution is acidified to pH 4.0, diluted 5-fold with water, and directly loaded onto a Waters C18 preparative column (2 inches diameter, 15–20 μm particle size, 300 Å pore size). The loaded column is eluted with a two-component eluent applied as a linear gradient, starting with 15% of solution A in solution B and finishing with 40% of solution A in solution B. Solution A is 0.1% TFA in $H_2O$ and solution B is 0.1% TFA in $CH_3CN$. Fractions exhibiting purity equal to or better than that desired are pooled and lyophilized to render the purified, trifluoroacetyl-protected product as the trifluoroacetate salt.

(7) Removal of the Trifluoroacetyl Protecting Group

The pure, (ε-TFA)-Lys-protected peptide is dissolved in a mixture of dioxane-water (1:1) and the resulting solution is diluted 2-fold with 0.2N $NaOH_{aq}$. After 15 minutes the mixture is acidified to pH 4.0, diluted 3-fold with water, and directly loaded onto a Waters C18 preparative column (2 inches diameter, 15–20 μm particle size, 300 Å pore size). The loaded column is eluted with a two-component eluent applied as a linear gradient, starting with 15% of solution A in solution B and finishing with 40% of solution A in solution B. Solution A is 0.1% TFA in $H_2O$ and solution B is 0.1% TFA in $CH_3CN$. Fractions exhibiting purity equal to or better than that desired are pooled and lyophilized to render the purified, final product as the trifluoroacetate salt.

EXAMPLE VI

Synthesis of:

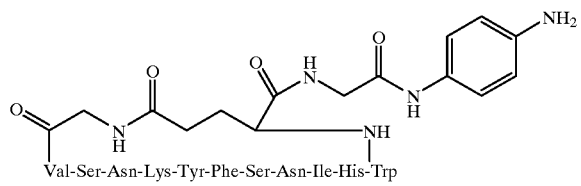
Val-Ser-Asn-Lys-Tyr-Phe-Ser-Asn-Ile-His-Trp

The starting material:

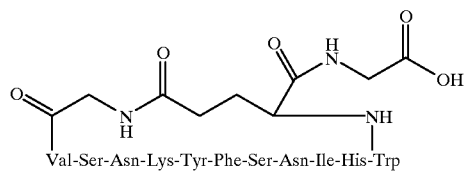
Val-Ser-Asn-Lys-Tyr-Phe-Ser-Asn-Ile-His-Trp was synthesized as described in commonly owned U.S. application Ser. No. 08/747,915. Two mg were dissolved in 100 mM MES pH 5.0 (0.5 mL) to a final concentration of 2.5 mM (4 mg/mL). Stock solutions of p-phenylenediamine (PPD; 10 mg/mL) and 1-Ethyl-3-(3-dimethylaminopropyl) carbodiimide (EDC; 10 mg/mL) were also prepared in 100 mM MES pH 5.0. EDC (50 μL of 10 mg/mL stock) and PPD (100 μL of 10 mg/mL stock) were added to 0.5 mL of the starting material solution, resulting in a molar ratio of approximately 2:2:1 (EDC: PPD: starting material). The mixture was allowed to incubate for 3 hours at room temperature, followed by HPLC purification on a $C_8$ reverse-phase column (linear gradient over 30 minutes; mobile phase A: 100% $H_2O$/0.1% TFA; mobile phase B: 100% acetonitrile/0.1% TFA). Under these conditions, the reaction goes to greater than 90% completion, yielding the desired product (RTLPPD) as the major component.

The synthesis of the isomer (RTLMPD) incorporating m-phenylenediamine (MPD) and the isomer (RTLOPD) incorporating o-phenylenediamine (OPD) followed this same scheme and gave similar yields.

EXAMPLE VII

Synthesis of:

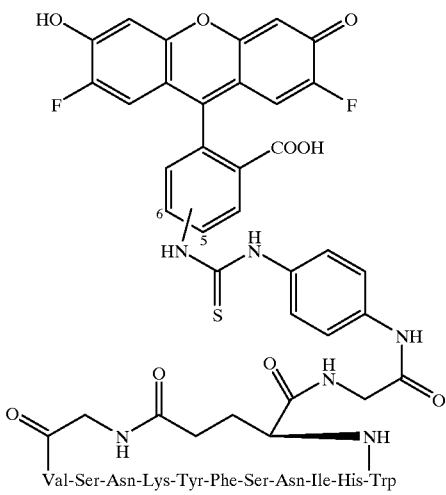
Val-Ser-Asn-Lys-Tyr-Phe-Ser-Asn-Ile-His-Trp

RTLPPD was synthesized as in Example VI. One mg was dissolved in 100 mM Phosphate Buffer pH 6.8 (1.5 mL) to a final concentration of 0.38 mM. Oregon Green (Difluorofluorescein isothiocyanate; 10 mg) was dissolved in DMSO (1 mL). Oregon Green (20 μL) was added to the RTLPPD solution (0.5 mL) in a polypropylene Eppendorf tube. The tube was wrapped in foil and the mixture was incubated on a rocker table for 6 hours at 22° C. The Oregon Green-labeled product was purified by HPLC using the same conditions as described in Example VI. Since the Oregon Green isothiocyanate precursor is a mixture of two positional isomers at 5 and 6, so too is the product.

EXAMPLE VIII

Synthesis of:

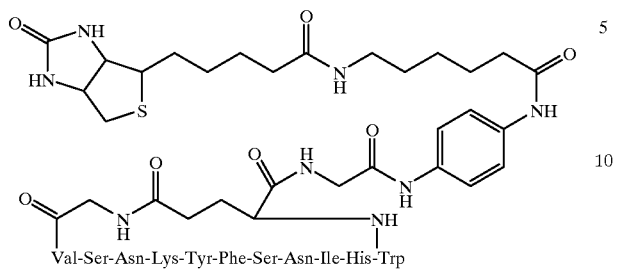

Val-Ser-Asn-Lys-Tyr-Phe-Ser-Asn-Ile-His-Trp

RTLPPD (1 mg) was dissolved in 100 mM Phosphate Buffer pH 6.8 (1.5 mL) to a final concentration of 0.38 mM. Biotin-X-sulfoNHS (where X is a 7-atom spacer; 10 mg) was dissolved in this same buffer (1 mL). Biotin-X-sulfoNHS (20 μL) was then added to the RTLPPD solution (0.5 mL) in a polypropylene Eppendorf tube and the mixture was incubated on a rocker table for 3 hours at 22° C. Excess, non-reacted Biotin-X-NHS was removed from the mixture by dialysis using a 2000 molecular weight cutoff membrane. The product was further purified by HPLC as described in Example VI.

EXAMPLE IX

Synthesis of:

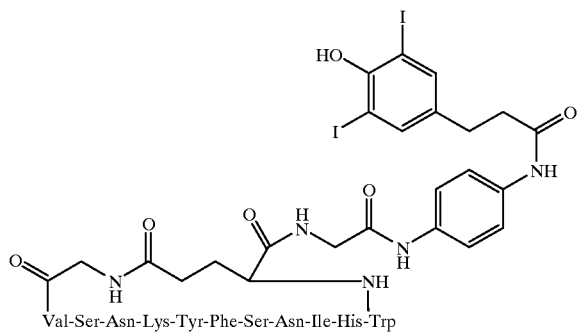

Val-Ser-Asn-Lys-Tyr-Phe-Ser-Asn-Ile-His-Trp

Bolton-Hunter reagent (N-succinimidyl-3-[4-hydroxyphenyl]-propionate) (10 mg) was dissolved in DMSO (1 mL) to a final concentration of 38 mM, then diluted 1:10 in 100 mM phosphate buffer pH 6.8. The diluted Bolton-Hunter solution (100 μL) was then added to a test tube precoated with IODO-GEN®. IODO-GEN® is a solid-Phase iodinating reagent which catalyzes the incorporation of iodine into Bolton-Hunter reagent. NaI was dissolved in water to a final concentration of 400 mM. This NaI solution (10 μL) was then added to the IODO-GEN®-coated tube containing the Bolton-Hunter solution and the iodination was allowed to proceed for 10 minutes at room temperature. RTLPPD (1 mg) was dissolved in 100 mM Phosphate Buffer pH 6.8 (1.5 mL) to a final concentration of 0.38 mM. The iodinated Bolton-Hunter reagent solution (0.1 mL) was removed from the IODO-GEN® tube and immediately added to the RTLPPD solution (0.5 mL) in a polypropylene Eppendorf tube. The mixture was incubated on a rocker table for 3 hours at 22° C. The product was purified by HPLC as described in Example VI. Any desired isotope of iodine can be used for the synthesis of the above compound by substituting $Na^{123}I$, $Na^{125}I$ or $Na^{131}I$ for NaI.

EXAMPLE X

Synthesis of:

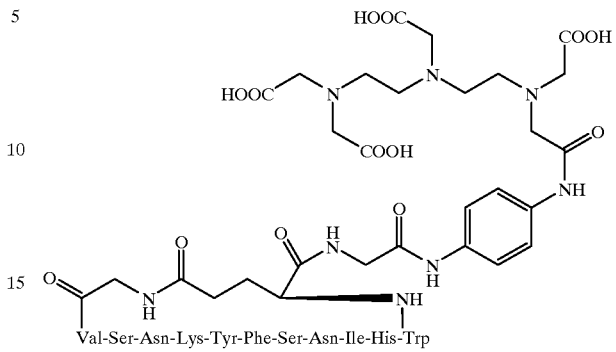

Val-Ser-Asn-Lys-Tyr-Phe-Ser-Asn-Ile-His-Trp

RTLPPD (1 mg) was dissolved in 100 mM Phosphate Buffer pH 6.8 (1.5 mL) to a final concentration of 0.38 mM. DTPA anhydride (Diethylenetriaminepentaacetic acid anhydride, 1 mg) was then added to the RTLPPD solution (0.5 mL) in a polypropylene Eppendorf tube and the mixture was incubated on a rocker table for 3 hours at 22° C. The product was purified by HPLC as described in Example VI.

EXAMPLE XI

Binding of the Cyclic Peptides to RKO Cells

The compounds of the invention were tested for their binding to uPAR by measuring their ability to inhibit the binding of [$^{125}$I]DFP-uPA (catalytically inactivated high molecular weight uPA) to uPAR expressed by RKO (human colon carcinoma) cells. Cells (about $5\times10^4$/well) were plated (in MEM with Earle's salts/10% FBS+antibiotics) in 24-well plates, then incubated in a humid 5% $CO_2$ atmosphere until the cells reach 70% confluence. Catalytically inactivated high molecular weight uPA (DFP-uPA) was radioiodinated using IODO-GEN® (Pierce) to a specific activity of about 250,000 cpm/mg. The cell-containing plates were then chilled on ice and the cells were washed twice (5 minutes each) with cold PBS/0.05% Tween-80. Test compounds were serially diluted in cold PBS/0.1% BSA/0.01% Tween-80 and added to each well to a final volume of 0.3 mL 10 minutes prior to the addition of the [$^{125}$I]DFP-uPA. Each well then receives 9500 cpm of [$^{125}$I]DFP-uPA at a final concentration of 0.2 nM. The plates were incubated at 4° C. for 2 hrs, after which time the cells were washed 3×(5 minutes each) with cold PBS/0.05% Tween-80. NaOH (1N; 0.5 mL) was added to each well to lyse the cells, the contents of each well were aspirated and the total counts in each well determined using a gamma counter. Each compound was tested in triplicate and the results are expressed as a percentage of the total radioactivity measured in wells containing [$^{125}$I]DFP-uPA alone, which is taken to represent maximum (100%) binding.

Figure 3:
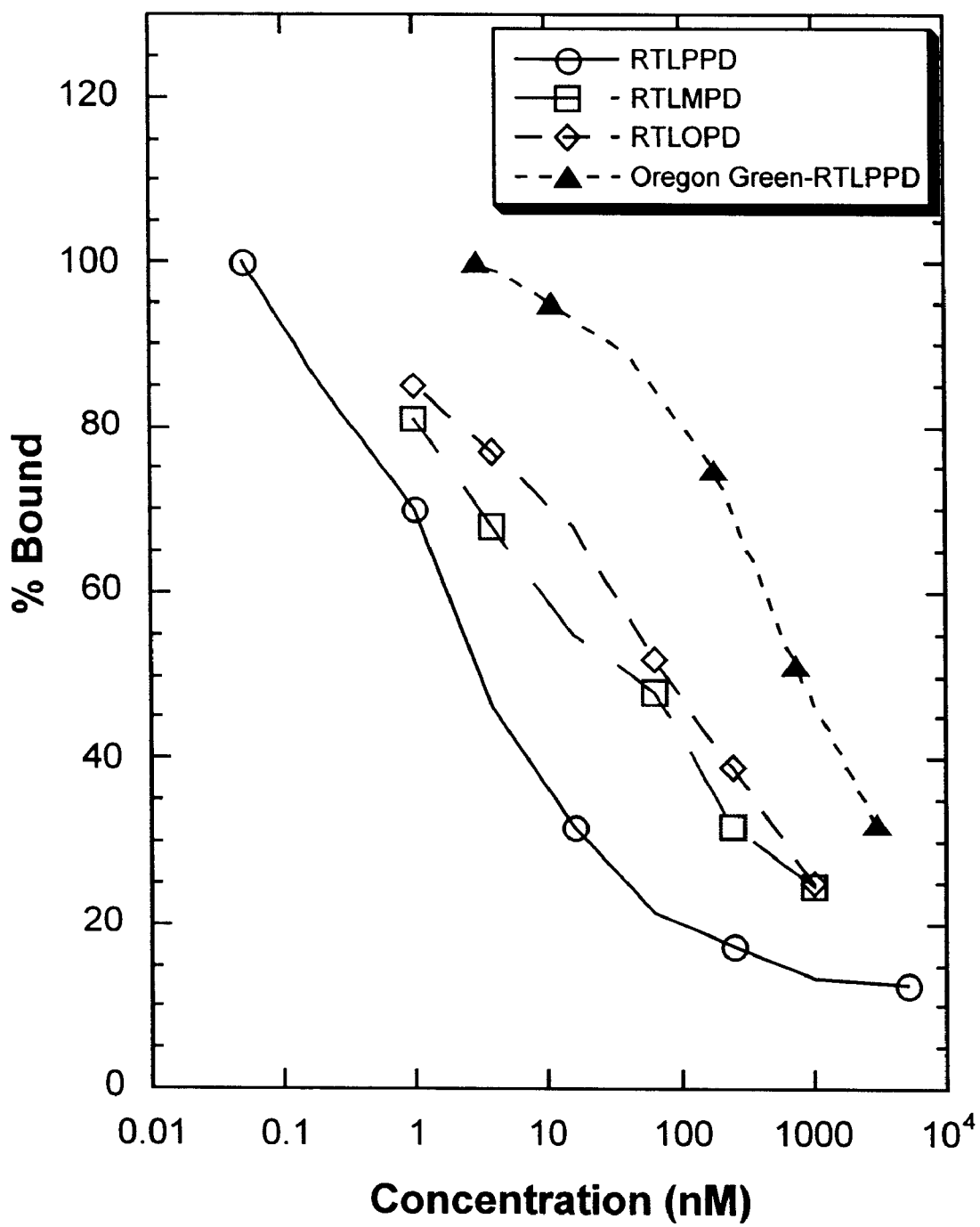
FIG. 3 is a graph showing the binding of the three compounds of Example VI and the compound of Example VII to RKO human colon carcinoma cells. The peptide of Example VI in which $R^2$=p-phenylene is termed "receptor targeting ligand-p-phenylenediamine derivative" (RTLPPD). When $R^2$=m-phenylene the resulting compound is termed RTLMPD. When $R^2$=o-phenylene the resulting compound is termed RTLOPD. The compound of Example VII is Oregon Green-modified-RTLPPD.
Figure 4:
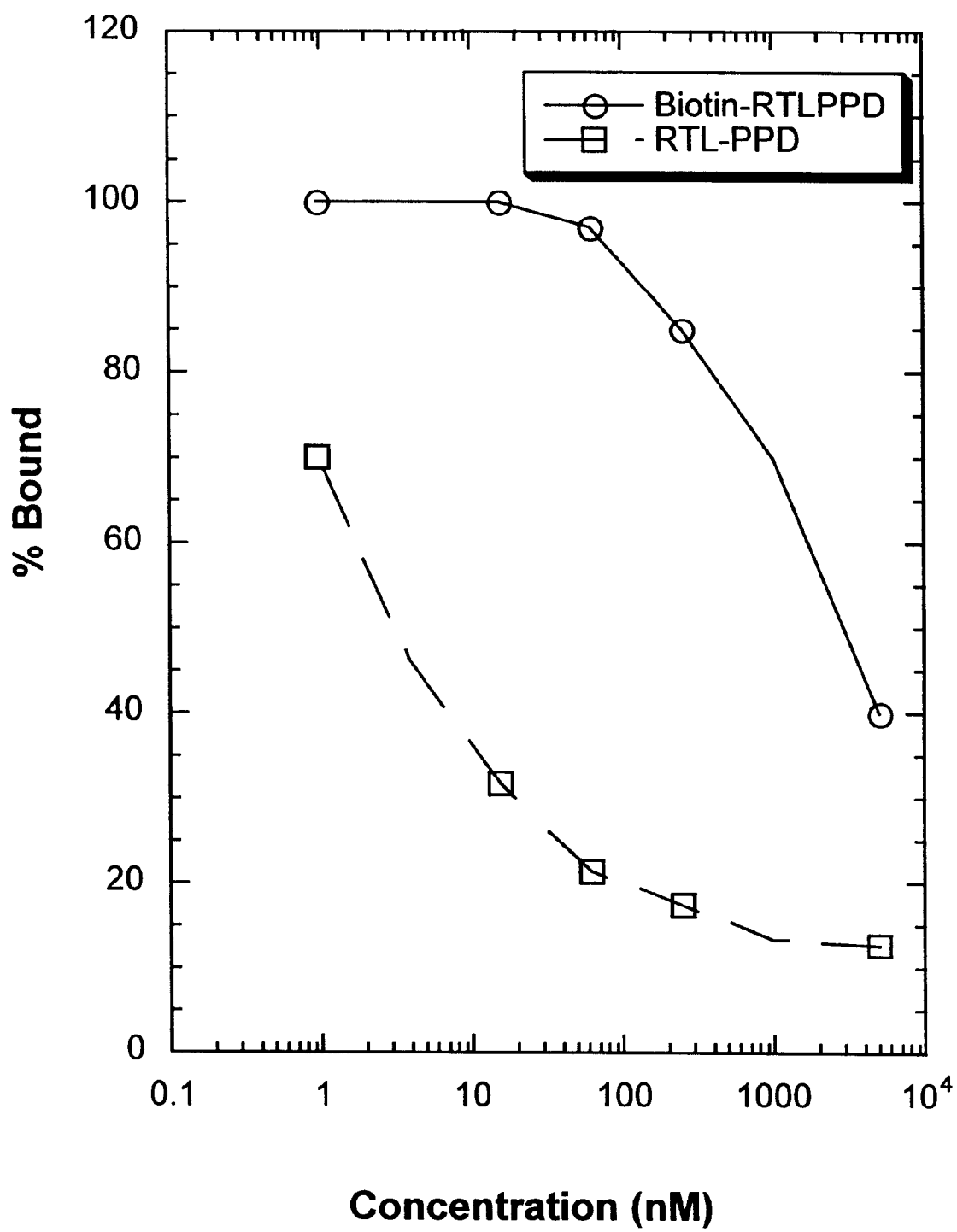
FIG. 4 is a graph showing the binding of a compound of Example VIII, biotin-modified-RTLPPD, to RKO human colon carcinoma cells.

RTLPPD inhibited the binding of [$^{125}$I]DFP-uPA with an $IC_{50}$ of approximately 5 nM (FIG. 3). Modification of RTLPPD with Oregon Green shifted the $IC_{50}$ to approximately 800 nM (FIG. 3) and modification with biotin shifted the $IC_{50}$ to approximately 1.1 µM (FIG. 4). RTLMPD and RTLOPD inhibited the binding of [$^{125}$I]DFP-uPA to RKO cells with an $IC_{50}$ of approximately 50 and 100 nM, respectively (FIG. 3).

EXAMPLE XII

Inhibition of PC-3 tumor cell invasion

Figure 5:
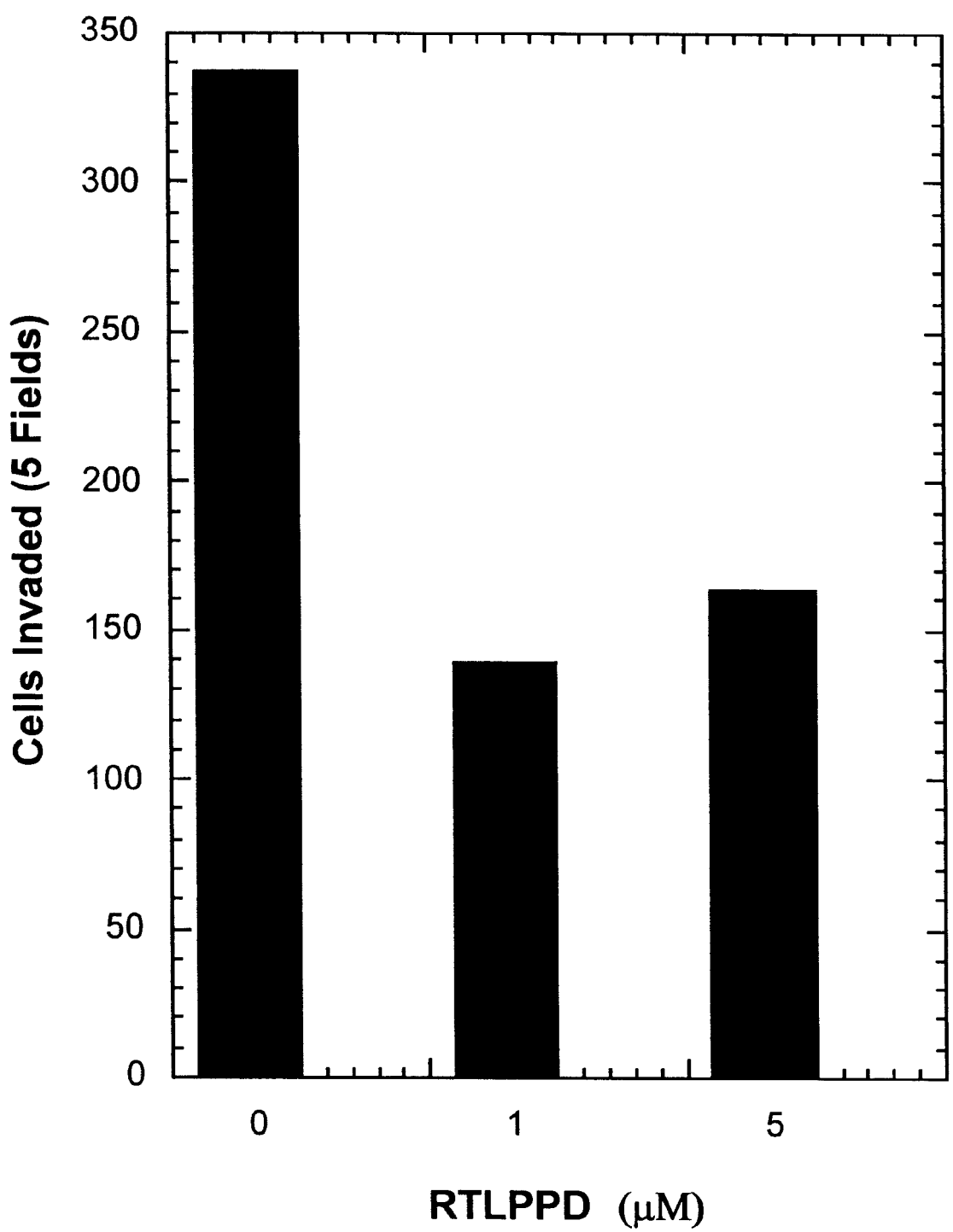
FIG. 5 is a graph showing the inhibition of PC-3 cell invasion by RTLPPD.

The ability of PC-3 (human prostatic carcinoma) cells to invade through a reconstituted basement membrane (Matrigel®) was measured using transwell tissue culture inserts. Transwells (Costar) containing polycarbonate membranes (8.0 µm pore size) were coated with Matrigel® (Collaborative Research), which had been diluted in sterile PBS to a final concentration of 75 µg/mL (60 AL of diluted Matrigel® per insert), and placed in the wells of a 24-well plate. The membranes were dried overnight in a biological safety cabinet, then rehydrated by adding 100 µL of DMEM containing antibiotics for 1 hour on a shaker table. The DMEM was removed from each insert by aspiration and 0.8 mL of DMEM/10% FBS/antibiotics was added to the lower chamber of each well of a 24-well plate. Fresh DMEM/antibiotics (100 µL), human Glu-plasminogen (5 µg/mL), and RTLPPD (1 µM and 200 nM) were added to the upper chamber. Tumor cells were trypsinized and resuspended in DMEM/antibiotics, then added to the top chamber of the transwell at a final concentration of 800,000 cells/mL. The final volume of the upper chamber was adjusted to 200 µL and the assembled plate was incubated in a humid 5% $CO_2$ atmosphere for 72 hours. After incubation, the cells were fixed and stained using DiffQuik® (Giemsa stain). The upper chamber was then scraped using a cotton swab to remove the Matrigel® and any cells which did not invade through the membrane- The membranes were detached from the transwell using an X-acto® blade, mounted on slides using Permount® and cover-slips, then counted under a high-powered (400×) field. An average of the cells invaded was determined from 5 fields counted and plotted as a function of inhibitor concentration. RTLPPD inhibited the invasion of PC-3 cells by greater than 50% at both concentrations tested (FIG. 5).

EXAMPLE XIII

Oregon Green-labeled-RTLPPD Targeting to Stimulated Endothelial Cells

Figure 6:
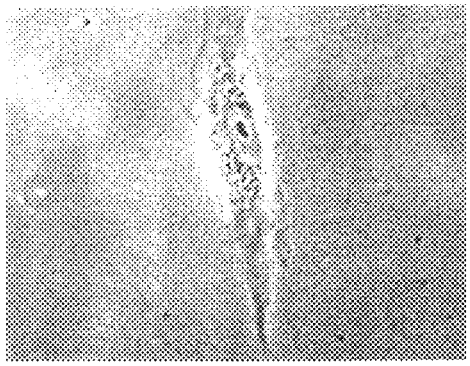
FIG. 6 is a series of photomicrographs showing immunofluorescence detection of Oregon Green-modified-RTLPPD binding to stimulated endothelial cells. Top panels: phase micrographs; bottom panels: corresponding fluorescence micrographs.
Figure 6:
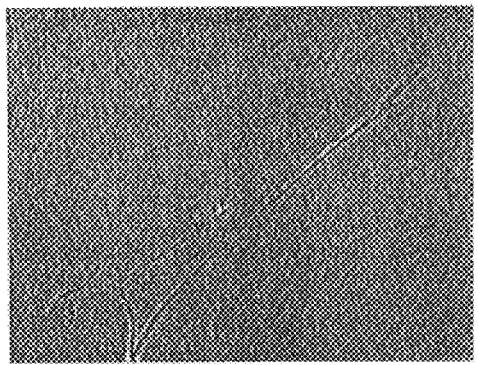
Figure 6:
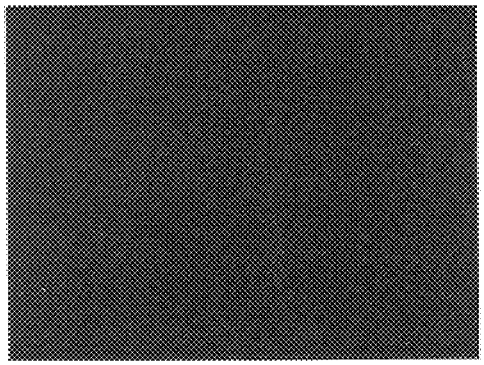
Figure 6:
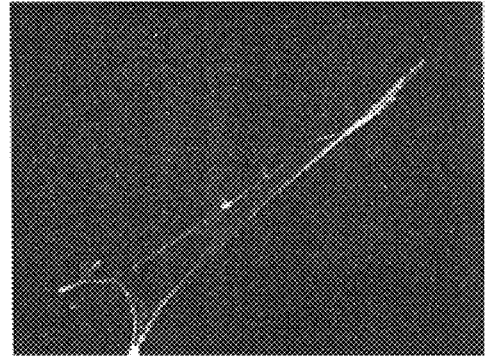

The ability of Oregon Green-labeled—RTLPPD to localize to stimulated endothelial cells was assessed by fluorescence microscopy. HUVECs were cultured for 24 hours on coverslips (in a 6-well plate) in the presence (10 ng/mL FGF-2 and 10 ng/mL VEGF) and absence of angiogenic stimulators, as might typically be found in a tumor. Oregon Green-labeled-RTLPPD (1 µM) was added to each well and allowed to incubate in the presence of the cells. The coverslips were removed from the wells and washed twice (5 minutes per wash) with PBS in a second 6-well plate. The coverslips were mounted onto slides and the fluorescence observed using a fluorescent microscope. Digitized images were captured using a video camera and NIH image. Binding of Oregon Green-labeled—RTLPPD was only observed to the stimulated cells. Furthermore, the binding pattern observed with Oregon Green-labeled-RTLPPD localized to the pseudopodia and focal adhesions of the cells, consistent with the previously described distribution of uPAR on migrating or adherent cell surfaces (FIG. 6).

EXAMPLE XIV

Inhibition of Angiogenesis In Vivo by uPAR-targeting Ligands

Angiogenesis induced by tumor growth and metastasis in vivo is examined in the models systems described above. Mice injected with 3LL cells are treated either with the cyclic peptide derivative or with vehicle and are sacrificed at various time points. Angiogenesis is assessed by determining microvessel density (MVD) using an antibody specific for microvascular endothelium or other markers of growing blood vessels, such as PECAM (CD31). Such an antibody is employed in conventional immunohistological methods to immunostain tissue sections as described by Penfold et al., *Br. J. Oral and Maxill. Surg.* 34: 37–41. A large number of such antibodies is commercially available, for example the JC70 mAb. The MVD is correlated with other measures of tumor behavior including lymph node status and primary tumor size and rate of growth. In humans as reported by Penfold et al., supra, tumor MVD correlates with lymph node metastasis and is independent of tumor size, growth rate or type of histological differentiation. Only MVD showed a significant association with lymph node metastasis.

The compounds are given i.p. Typical dosages are 4–10 mg/kg/day. At various time points, two animals are sacrificed, and the tumor tissue and surrounding tissue is prepared for histological examination. Results are reported as the average microvessel density of 5 fields each from 5 different sections.

The cyclic peptide derivative of Example VI, comprising the natural uPA sequence at positions $X^1$ through $X^{11}$ corresponding to the mouse sequence [SEQ ID NO:4] was cyclized using the L10 linker ($R^2$=p-phenylene). This compound is termed "murine RTLPPD." In mice treated with murine RTLPPD, there is a significant reduction in the number of microvessels in the region of the primary tumor at the subcutaneous inoculation site as compared to controls. Control cyclic peptides in this and subsequent examples have the Tyr, Phe and (in the case of human, Trp) positions replaced with Ala residues. Such peptides have no detectable binding to uPAR. Here, cyclic peptide derivatives having the Ala substitutions have no significant effect on angiogenesis. Therefore, murine RTLPPD has anti-angiogenic activity which is responsible at least in part for its effectiveness as an antitumor agent.

Additional compounds having the L10 linker and either o- or m-phenylenediamine are tested in this model, as are cyclic peptides comprising the other L groups disclosed above, and having p-, o- or m-phenylene as the $R^2$ group and have similar biological effects in vivo. Similar effects are observed using the substituted amino acid sequences described above. Murine RTLPPD and its derivatives to which $^{131}$I is conjugated (either 1 or 2 I atoms per molecule of cyclic peptide) are effective radiotherapeutics and are found to be at least two-fold more potent than their unconjugated analogues.

EXAMPLE XV

Inhibition of Spontaneous Metastasis In Vivo by uPAR-targeting Ligand Derivatives The rat syngeneic breast cancer system (Xing et al., *Int. J. Cancer* 67:423–429 (1996) employs Mat BIII rat breast cancer cells. Tumor cells, 1×10⁶ suspended in 0.1 mL PBS are inoculated into the mammary fat pads of 10 female Fisher rats. At the time of inoculation, a 14-day Alza osmotic mini-pump is implanted intraperitoneally to dispense the peptide. The peptide is dissolved in PBS (200 mM stock), sterile filtered and placed in the minipump to achieve a dispensing rate of about 4 mg/kg/day. Control animals receive vehicle (PBS) alone or an Ala-substituted control peptide in the minipump. Animals are euthanized at day 14.

In this study uPAR-targeting ligands are made based on the rat amino acid sequences of the uPAR-binding domain of uPA. Thus in parallel to human sequence RTLPPD, the following compound, "rat RTLPPD" is tested:

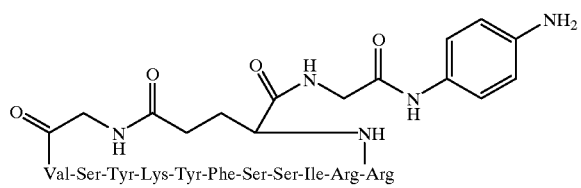

Val-Ser-Tyr-Lys-Tyr-Phe-Ser-Ser-Ile-Arg-Arg

In the rats treated with this and related cyclic peptide derivatives, there is a significant reduction in the size of the primary tumor and in the number of metastases in the spleen, lungs, liver, kidney and lymph nodes (enumerated as discrete foci). Upon histological and immunohistochemical analysis, it is seen that in treated animals, there is increased necrosis and signs of apoptosis. Large necrotic areas are seen in tumor regions lacking in neovascularization. Rat RTLPPD and its derivatives to which $^{131}I$ is conjugated (either 1 or 2 I atoms per molecule of cyclic peptide) are effective radiotherapeutics and are found to be at least two-fold more potent than their unconjugated analogues.

In contrast, treatment with control cyclic peptides failed to cause a significant change in tumor size or metastasis.

EXAMPLE XVI

Inhibition of Growth of Human Tumors In Vivo by uPAR-targeting Ligand Derivatives The ability of the uPAR-targeting cyclic peptides are tested for their ability to inhibit the local growth of a human tumor in a nude mouse model, as described above. Nude mice are inoculated s.c. in their right flanks with 1×10⁶ cells MDA-MB-231 human breast carcinoma cells and Matrigel® in a volume of 0.2 mL). The tumors are staged to 200 mm³ and then treatment with the test compounds of the invention is started (100 gg/animal/day given q.d. I.P). Tumor volumes are measured every other day and the animals are sacrificed after 3 weeks of treatment. The tumors are excised, weighed and paraffin embedded. Histological sections of the tumors are analyzed histochemically. In mice treated with RTLPPD, there is a significant lower tumor volume compared to vehicle controls and subjects treated with a control cyclic peptide. Therefore, RTLPPD has direct antitumor effects. Histological analysis shows that this agent induced apoptosis in the tumor cells.

Compounds having the L10 linker and either o- or m-phenylenediamine are tested in this model, as are cyclic peptides comprising the other L groups disclosed above, and having p-, o- or m-phenylene as the R² group. All these compounds have similar anti-tumor effects in vivo. Similar effects are observed using the substituted amino acid sequences described above. RTLPPD and its derivatives to which $^{131}I$ is conjugated (either 1 or 2 I atoms per molecule of cyclic peptide) are effective radiotherapeutics and are found to be at least two-fold more potent than their unconjugated analogues.

EXAMPLE XVII

Inhibition of Experimental Metastasis of Tumor Cells In Vivo by uPAR-Targeting Ligand Derivatives The cyclic peptide derivatives described above are also tested for efficacy in vivo in a model of human tumor metastasis in nude mice. PC-3 cells transfected with the gene encoding the enzyme chloramphenicol acetyl-transferase (CAT) are inoculated into nude mice i.v. at doses of 1×10⁶ cells per mouse. These mice are implanted with a minipump, as above, which dispenses 4 mg/kg/day of the peptide or vehicle over a period of 14 or 21 days. At termination of treatment, the animals are euthanized and the tumor marker probe CAT is assayed in regional lymph nodes, femurs, lungs, and brain.

In the mice treated with RTLPPD, but not with vehicle or control cyclic peptides, the number and size of metastatic foci is markedly inhibited. RTLPPD and its derivatives to which $^{131}I$ is conjugated (either 1 or 2 I atoms per molecule of cyclic peptide) are effective radiotherapeutics and are found to be at least two-fold more potent than their unconjugated analogues. These results indicate that these uPAR-targeting cyclic peptide derivatives interfere with the metastatic process.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A uPAR-targeting cyclic peptide compound of formula

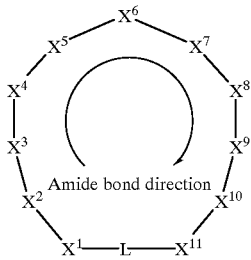

wherein each of $X^1$ through $X^{11}$ is a D- or L-amino acid, $X^1$ is Val, Ala, Met, Cys, HomoCys, Glu, Asp, GluR$^1$, AspR$^1$ or Ile;

$X^2$ is Ser, Ala, Cys, HomoCys, Glu, Asp, GluR$^1$, AspR$^1$ or Thr;

$X^3$ is Asn, Gln or Tyr;

$X^4$ is Lys, Arg or His;

$X^5$ is Tyr, Trp, Phe, substituted Phe, di-substituted Phe, HomoPhe, β-(3-pyridyl)alanine, β-(2-thienyl)alanine, β-(1-naphthyl)-alanine or β-(2-naphthyl)alanine;

$X^6$ is Phe, Tyr, Tip, substituted Phe, di-substituted Phe, HomoPhe, β-(3-pyridyl)alanine, β-(2-thienyl)alanine, β-(1-naphthyl)alanine or β-(2-naphthyl)alanine;

$X^7$ is Ser, Cys, HomoCys, Glu, Asp, GluR, AspR$^1$ or Ala;

$X^8$ is Asn, Ala, Ser, Arg, Cys, HomoCys, Glu, Asp, GluR$^1$, AspR$^1$ or Gln;

$X^9$ is Ile, Leu, Val, NorVal or NorLeu;

$X^{10}$ is His, Ala, Arg, Gln, Cys, HomoCys, Glu, Asp, GluR$^1$, AspR$^1$ or Lys;

$X^{11}$ is Trp, Tyr, Arg, Phe, substituted Phe, di-substituted Phe, HomoPhe, β-(3-pyridyl)alanine, β-(2-thienyl)alanine, β-(1-naphthyl)alanine, or β-(2-naphthyl)alanine;

with the proviso that at least one of $X^1$, $X^2$, $X^7$, $X^8$ or $X^{10}$ is selected from the group consisting of Cys, HomoCys, Glu, Asp, GluR$^1$ and AspR$^1$, wherein R$^1$ is an organic diamino group —NH—R$^2$—NH$_2$ bonded to the side chain carbonyl of Glu or Asp, and wherein R$^2$ is, (a) p-phenylene, o-phenylene or m-phenylene;

(b) —O—(CH$_2$)$_x$—O— wherein x≧2; or (c) —CH$_2$—CO—NH—(CH$_2$)$_x$—NH—CO—CH$_2$— wherein x>2, said diamino group having the following properties:

(i) the pK$_a$ of each NH$_2$ group in a parent diamine H$_2$N—R$^2$—NH$_2$ of said R$^1$ diamino group —NH—R$^2$13 NH$_2$ is less than about 8.0, and 0

(ii) the pK$_a$ of the NH$_2$ group in said R$^1$ group is less than about 8.0, and L is a linking unit, such that when $X^1$ and $X^{11}$ are linked, the line dimension between the C$^\alpha$ carbon of amino acid $X^1$ and the C$^\alpha$ carbon of amino acid $X^{11}$ is between about 4 and 12 Ångstrom units.

2. The compound of claim 1 wherein at least two of $X^1$, $X^2$, $X^7$, $X^8$ or $X^{10}$ are selected from the group consisting of Cys, HomoCys, Glu, Asp, GluR$^1$ and AspR$^1$.

3. The compound of claim 1 wherein the linear dimension between the C$^\alpha$ carbon of amino acid $X^1$ and the C$^\alpha$ carbon of amino acid $X^{11}$ is between about 5 and 10 Ångstrom units.

4. The compound of claim 3 wherein the linear dimension between the C$^\alpha$ carbon of amino acid $X^1$ and the C$^\alpha$ carbon of amino acid $X^{11}$ is between about 6 and 8 Ångstrom units.

5. The compound of claim 1 wherein L is a linker that, reading in the direction $X^1$-L-$X^{11}$, is selected from the group consisting of:

L1 —CO—CH$_2$—NH—CO—CH$_2$—CH$_2$—CH (CO—NH—CH$_2$—CO—NH$_2$)—NH—

L2 —CO—CH$_2$—NH—CO—CH$_2$—CH$_2$—CH (CO—NH—CH (CH$_2$SH)—CO—NH$_2$)—NH—

L3 —CO—CH (CH$_2$SH)—NH—CO—CH$_2$—CH$_2$—CH (CO—NH—CH$_2$—CONH$_2$)—NH—

L4 —CO—CH$_2$—NH—CO—CH$_2$—CH$_2$—CH (CO—NH—CH (CH$_2$CH$_2$SH)—CO—NH$_2$)—NH—

L5 —CO—CH (CH$_2$CH$_2$SH)—NH—CO—CH$_2$—CH$_2$—CH (CO—NH—CH$_2$—CONH$_2$)—NH—

L6 —CO—CH (CH$_2$CH$_2$COR$^1$)—NH—CO—CH$_2$—CH$_2$—CH (CO—NH—CH$_2$—CONH$_2$)—NH—

L7 —CO—CH (CH$_2$COR$^1$)—NH—CO—CH$_2$—CH$_2$—CH (CO—NH—CH$_2$—CONH$_2$)—NH—

L8 —CO—CH$_2$—NH—CO—CH$_2$—CH$_2$—CH (CO—NH—CH (CH$_2$CH$_2$COR$^1$)—CO—NH$_2$)—NH—

L9 —CO—CH$_2$—NH—CO—CH$_2$—CH$_2$—CH (CO—NH—CH (CH$_2$COR$^1$)—CO—NH$_2$)—NH—

L10 —CO—CH$_2$—NH—CO—CH$_2$—CH$_2$—CH (CO—NH—CH$_2$—COR$^1$)—NH—

L11 —CO—CH (CH$_2$CH$_2$COOH)—NH—CO—CH$_2$—CH$_2$—CH (CO—NH—CH$_2$—CONH$_2$)—NH—

L12 —CO—CH (CH$_2$COOH)—NH—CO—CH$_2$—CH$_2$—CH (CO—NH—CH$_2$—CONH$_2$)—NH—

L13 —CO—CH$_2$—NH—CO—CH$_2$—CH$_2$—CH (CO—NH—CH (CH$_2$CH$_2$COOH)—CO—NH$_2$)—NH—; and

L14 —CO—CH$_2$—NH—CO—CH$_2$—CH$_2$—CH (CO—NH—CH (CH$_2$COOH)—CO—NH$_2$)—NH— wherein R$^1$ in any of L6 to L10 is a diamino group —NH—R$^2$—NH$_2$, and R$^2$ is (a) p-phenylene, o-phenylene or m-phenylene, (b) —O—CH(CH$_2$)$_x$—O—, with x≧2; or (c) —CH$_2$—CO—NH—(CH$_2$)$_x$—NH—CO—CH$_2$— with x≧2, said diamino group having the following properties:

(i) the pK$_a$ of each NH$_2$ group in a parent diamine H$_2$N—R$^2$—NH$_2$ of said R$^1$ group —NH—R$^2$—NH$_2$ is less than about 8.0; and (ii) the pK$_a$ of the NH$_2$ group in said —NH—R$^2$—NH$_2$ is less than about 8.0.

6. A uPAR-targeting cyclic peptide compound of formula

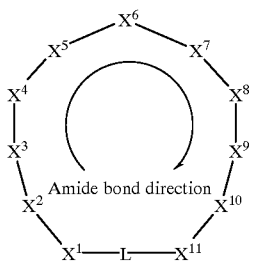

wherein:

each of $X^1$ through $X^{11}$ is a D- or L-amino acid,

L is a linking unit that, reading in the direction $X^1$-L-$X^{11}$, is selected from the group consisting of:

L1 —CO—CH$_2$—NH—CO—CH$_2$—CH$_2$—CH(CO—NH—CH$_2$—CO—NH$_2$)—NH—;

L2 —CO—CH$_2$—NH—CO—CH$_2$—CH$_2$—CH(CO—NH—CH(CH$_2$SH)—CO—NH$_2$)—NH—;

L3 —CO—CH(CH$_2$SH)—NH—CO—CH$_2$—CH$_2$—CH(CO—NH—CH$_2$—CONH$_2$)—NH—;

L4 —CO—CH$_2$—NH—CO—CH$_2$—CH$_2$—CH(CO—NH—CH(CH$_2$CH$_2$SH)—CO—NH$_2$)—NH—;

L5 —CO—CH(CH$_2$CH$_2$SH)—NH—CO—CH$_2$—CH$_2$—CH(CO—NH—CH$_2$—CONH$_2$)—NH—;

L6 —CO—CH(CH$_2$CH$_2$COR$^1$)—NH—CO—CH$_2$—CH$_2$—CH(CO—NH—CH$_2$—CONH$_2$)—NH—;

L7 —CO—CH(CH$_2$COR$^1$)—NH—CO—CH$_2$—CH$_2$—CH(CO—NH—CH$_2$—CONH$_2$)—NH—;

L8 —CO—CH$_2$—NH—CO—CH$_2$—CH$_2$—CH(CO—NH—CH(CH$_2$CH$_2$COR$^1$)—CO—NH$_2$)—NH—;

L9 —CO—CH$_2$—NH—CO—CH$_2$—CH$_2$—CH(CO—NH—CH(CH$_2$COR$^1$)—CO—NH$_2$)—NH—;

L10 —CO—CH$_2$—NH—CO—CH$_2$—CH$_2$—CH(CO—NH—CH$_2$—COR$^1$)—NH—;

L11 —CO—CH(CH$_2$CH$_2$COOH)—NH—CO—CH$_2$—CH$_2$—CH(CO—NH—CH$_2$—CONH$_2$)—NH—;

L12 —CO—CH(CH$_2$COOH)—NH—CO—CH$_2$—CH$_2$—CH(CO—NH—CH$_2$—CONH$_2$)—NH—;

L13 —CO—CH$_2$—NH—CO—CH$_2$—CH$_2$—CH(CO—NH—CH(CH$_2$CH$_2$COOH)—CO—NH$_2$)—NH—; and

L14 —CO—CH$_2$—NH—CO—CH$_2$—CH$_2$—CH(CO—NH—CH(CH$_2$COOH)—CO—NH$_2$)—NH—;

$X^3$ is Asn, Gln or Tyr;

$X^4$ is Lys, Arg or His;

$X^5$ is Tyr, Trp, Phe, substituted Phe, di-substituted Phe, HomoPhe, β-(3-pyridyl)alanine, β-(2-thienyl)alanine, β-(1-naphthyl)-alanine, or β-(2-naphthyl)alanine;

$X^6$ is Phe, Tyr, Trp, substituted Phe, di-substituted Phe, HomoPhe, β-(3-pyridyl)alanine, β-(2-thienyl)alanine, β-(1-naphthyl)alanine, or β-(2-naphthyl)alanine;

$X^9$ is Ile, Leu, Val, NorVal or NorLeu;

$X^{11}$ is Trp, Tyr, Arg, Phe, substituted Phe, di-substituted Phe, HomoPhe, β-(3-pyridyl)alanine, β-(2-thienyl)alanine, β-(1-naphthyl)alanine, or β-(2-naphthyl)alanine;

with the proviso that, when the linker L is any of L2 to L14, $X^1$ is Val, Ala, Met or Ile;

$X^2$ is Ser, Ala or Thr;

$X^7$ is Ser or Ala;

$X^8$ is Asn, Ala, Ser, Arg or Gln; and $X^{10}$ is His, Ala, Arg, Gln or Lys;

but when the linker L is L1, at least one of $X^1$, $X^2$, $X^7$, $X^8$ or $X^{10}$ is selected from the group consisting of Cys, HomoCys, Glu, Asp, GluR$^1$ and AspR$^1$, whereas the amino acid residue at each of the remaining positions of $X^1$, $X^2$, $X^7$, $X^8$ or $X^{10}$ is as above for the condition of L being any of L2 to L14, wherein R$^1$ in GluR$^1$, AspR$^1$ or in any of L6–L10 is a diamino group —NH—R$^2$—NH$_2$ that is bonded to the γ- or β-carbonyl of Glu or Asp, respectively, and R$^2$ is (a) p-phenylene, o-phenylene or m-phenylene;

(b) —O—CH$_2$)$_x$—O— (with x≥2; or (c) —CH$_2$—CO—NH—(CH$_2$)$_x$—NH—CO—CH$_2$— with x≥2, wherein said diamino group has the following properties:

(i) the pK$_a$ of each NH$_2$ group in a parent diamine H$_2$N—R$^2$—NH$_2$ of said R$^1$ group —NH—R$^2$—NH$_2$ is less than about 8.0, and (ii) the pK$_a$ of the NH$_2$ group in said R$^1$ group is less than about 8.0.

7. The compound of claim 1, 2, 5, or 6 wherein R$^2$ is p-phenylene, o-phenylene or m-phenylene.

8. The compound of claim 1, 2, 5 or 6 wherein $X^1$–$X^{11}$ is SEQ ID NO:2, L is L10 and R$^2$ is p-phenylene.

9. The compound of claim 1, 2, 5, or 6 wherein any one of $X^5$, $X^6$ or $X^{11}$ is substituted or disubstituted Phe.

10. The compound of claim 9 wherein said substituted or di-substituted Phe is substituted with a substituent selected from the group consisting of (a) a halo;

(b) a nitro;

(c) a C1–C6 straight or branched chain alkyl; and (d) in the case of disubstituted Phe, any two of (a)–(c).

11. The compound of claim 7 wherein any one of $X^5$, $X^6$ or $X^{11}$ is substituted or di-substituted Phe.

12. The compound of claim 11 wherein said substituted or di-substituted Phe is substituted with a substituent selected from the group consisting of (a) a halo;

(b) a nitro;

(c) a C1–C6 straight or branched chain alkyl; and (d) in the case of di-substituted Phe, any two of (a)–(c).

13. The compound of any one of claims 1, 2, 5 or 6 having an IC$_{50}$ value in a competitive binding assay to uPA receptor in vitro of less than about $10^{-5}$ molar.

14. The compound of claim 13 having an IC$_{50}$ value less than about $10^{-6}$ molar.

15. The compound of claim 14 having an IC$_{50}$ value less than about $10^{-7}$ molar.

16. A uPAR-targeting pharmaceutical composition comprising:

(a) the cyclic peptide compound of any of claims 1, 2, 3, 4, 5, 6; and (b) a pharmaceutically acceptable carrier.

17. A uPAR-targeting pharmaceutical composition comprising:

(a) the cyclic peptide compound of claim 7; and (b) a pharmaceutically acceptable carrier.

18. A uPAR-targeting pharmaceutical composition comprising:

(a) the cyclic peptide compound of claim 8; and (b) a pharmaceutically acceptable carrier.

19. A uPAR-targeting pharmaceutical composition comprising:

(a) the cyclic peptide compound of claim 9; and (b) a pharmaceutically acceptable carrier.

20. A uPAR-targeting pharmaceutical composition comprising:

(a) the cyclic peptide compound of claim 10; and (b) a pharmaceutically acceptable carrier.

21. A uPAR-targeting pharmaceutical composition comprising:

(a) the cyclic peptide compound of claim 11; and (b) a pharmaceutically acceptable carrier.

22. A uPAR-targeting pharmaceutical composition comprising:
(a) the cyclic peptide compound of claim 12; and
(b) a pharmaceutically acceptable carrier.

23. A uPAR-targeting pharmaceutical composition comprising:
(a) the cyclic peptide compound of claim 13; and
(b) a pharmaceutically acceptable carrier.

24. A uPAR-targeting pharmaceutical composition comprising:
(a) the cyclic peptide compound of claim 14; and
(b) a pharmaceutically acceptable carrier.

25. A uPAR-targeting pharmaceutical composition comprising:
(a) the cyclic peptide compound of claim 15; and
(b) a pharmaceutically acceptable carrier.

26. The pharmaceutical composition of claim 17 in a form suitable for injection.

27. The pharmaceutical composition of claim 18 in a form suitable for injection.

28. The pharmaceutical composition of claim 19 in a form suitable for injection.

29. The pharmaceutical composition of claim 20 in a form suitable for injection.

30. The pharmaceutical composition of claim 21 in a form suitable for injection.

31. The pharmaceutical composition of claim 22 in a form suitable for injection.

32. The pharmaceutical composition of claim 23 in a form suitable for injection.

33. The pharmaceutical composition of claim 24 in a form suitable for injection.

34. The pharmaceutical composition of claim 25 in a form suitable for injection.

35. A method for inhibiting cell migration, cell invasion, cell proliferation or angiogenesis, comprising contacting cells having uPAR with an effective amount of the compound of any of claims 1, 2, 5 or 6.

36. A method for inhibiting cell migration, cell invasion, cell proliferation or angiogenesis, comprising contacting cells having uPAR with an effective amount of the compound of claim 7.

37. A method for inhibiting cell migration, cell invasion, cell proliferation or angiogenesis, comprising contacting cells having uPAR with an effective amount of the compound of claim 8.

38. A method according to claim 35 wherein said cell invasion is by tumor cells.

39. A method according to claim 36 wherein said cell invasion is by tumor cells.

40. A method according to claim 37 wherein said cell invasion is by tumor cells.

41. A method for treating a subject having a disease or condition associated with the presence or activity of uPAR wherein the disease or condition is characterized by undesired cell migration, cell invasion, cell proliferation or angiogenesis, comprising administering to said subject, an effective amount of a pharmaceutical composition according to claim 16.

42. A method of treating a subject having a disease or condition associated with the presence or activity of uPAR wherein the disease or condition is characterized by undesired cell migration, cell invasion, cell proliferation or angiogenesis, comprising administering to said subject an effective amount of a pharmaceutical composition according to claim 25.

43. A method according to claim 41, wherein said disease or condition is tumor growth, invasion or metastasis.

44. A method for inhibiting cell migration, cell invasion, cell proliferation or angiogenesis comprising contacting cells having uPAR with an effective amount of the composition of claim 9.

45. A method for inhibiting cell migration, cell invasion, cell proliferation or angiogenesis comprising contacting cells having uPAR with an effective amount of the composition of claim 10.

46. A method for inhibiting cell migration, cell invasion, cell proliferation or angiogenesis comprising contacting cells having uPAR with an effective amount of the composition of claim 11.

47. A method for inhibiting cell migration, cell invasion, cell proliferation or angiogenesis comprising contacting cells having uPAR with an effective amount of the composition of claim 12.

48. A method according to claim 42, wherein said disease or condition is tumor growth, invasion or metastasis.

49. A method for treating a subject having a disease or condition associated with the presence or activity of uPAR wherein the disease or condition is characterized by undesired cell migration, cell invasion, cell proliferation or angiogenesis, comprising administering to said subject, an effective amount of a pharmaceutical composition according to claim 17.

50. A method according to claim 49, wherein said disease or condition is tumor growth, invasion or metastasis.

51. A method for treating a subject having a disease or condition associated with the presence or activity of uPAR wherein the disease or condition is characterized by undesired cell migration, cell invasion, cell proliferation or angiogenesis, comprising administering to said subject, an effective amount of a pharmaceutical composition according to claim 18.

52. A method according to claim 51 wherein said disease or condition is tumor growth, invasion or metastasis.

53. A method for treating a subject having a disease or condition associated with the presence or activity of uPAR wherein the disease or condition is characterized by undesired cell migration, cell invasion, cell proliferation or angiogenesis, comprising administering to said subject, an effective amount of a pharmaceutical composition according to claim 19.

54. A method according to claim 53, wherein said disease or condition is tumor growth, invasion or metastasis.

55. A method for treating a subject having a disease or condition associated with the presence or activity of uPAR wherein the disease or condition is characterized by undesired cell migration, cell invasion, cell proliferation or angiogenesis, comprising administering to said subject, an effective amount of a pharmaceutical composition according to claim 20.

56. A method according to claim 55, wherein said disease or condition is tumor growth, invasion or metastasis.

57. A method for treating a subject having a disease or condition associated with the presence or activity of uPAR wherein the disease or condition is characterized by undesired cell migration, cell invasion, cell proliferation or angiogenesis, comprising administering to said subject, an effective amount of a pharmaceutical composition according to claim 21.

58. A method according to claim 57, wherein said disease or condition is tumor growth, invasion or metastasis.

59. A method for treating a subject having a disease or condition associated with the presence or activity of uPAR wherein the disease or condition is characterized by undesired cell migration, cell invasion, cell proliferation or angiogenesis, comprising administering to said subject, an effective amount of a pharmaceutical composition according to claim 22.

60. A method according to claim 59, wherein said disease or condition is tumor growth, invasion or metastasis.

* * * * *

UNITED STATES PATENT AND TRADEMARK OFFICE
CERTIFICATE OF CORRECTION

PATENT NO. : 6,277,818 B1
DATED : August 21, 2001
INVENTOR(S) : Mazar et al.

It is certified that error appears in the above-identified patent and that said Letters Patent is hereby corrected as shown below:

<u>Title page,</u>
Item [57], ABSTRACT,
Line 5, please delete "between the a" and replace therfor with -- between the $\alpha$ --.

<u>Column 49,</u>
Line 46, please delete "p-phenylene, o-phenylene or m-phenylene;" and replace therefor with -- $p$-phenylene, $o$-phenylene or $m$-phenylene; --.
Line 47, please delete "$\geqq$" and replace therefor with -- $\geq$ --
Line 50, please delete "x>2" and replace therefor with -- $x \geq 2$ --.
Line 54, please delete "$R^2 13\ NH_2$", and replace therefor with -- $R^2\text{-}NH_2$ --.

<u>Column 50,</u>
Line 40, please delete "p-phenylene, o-phenylene or m-phenylene;" and replace therefor with -- $p$-phenylene, $o$-phenylene or $m$-phenylene; --.

<u>Column 51,</u>
Line 67, please delete "$\geqq$" and replace therefor with -- $\geq$ --

<u>Column 52,</u>
Line 2, please delete "$\geqq$" and replace therefor with -- $\geq$ --
Line 11, please delete "p-phenylene, o-phenylene or m-phenylene;" and replace therefor with -- $p$-phenylene, $o$-phenylene or $m$-phenylene; --.
Line 13, please delete "p-phenylene." and replace therefor with -- $p$-phenylene. --.

Signed and Sealed this

Twenty-fourth Day of August, 2004

JON W. DUDAS
*Director of the United States Patent and Trademark Office*